US012577540B2

(12) United States Patent
Alam

(10) Patent No.: US 12,577,540 B2
(45) Date of Patent: Mar. 17, 2026

(54) SUSPENSION MODE SEED TRAIN DEVELOPMENT FOR ADHERENT CELLS

(71) Applicant: Sarepta Therapeutics, Inc., Cambridge, MA (US)

(72) Inventor: Maroof Alam, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 340 days.

(21) Appl. No.: 18/255,221

(22) PCT Filed: Dec. 9, 2021

(86) PCT No.: PCT/US2021/062645

§ 371 (c)(1),
(2) Date: May 31, 2023

(87) PCT Pub. No.: WO2022/125793

PCT Pub. Date: Jun. 16, 2022

(65) Prior Publication Data

US 2024/0018487 A1     Jan. 18, 2024

Related U.S. Application Data

(60) Provisional application No. 63/123,602, filed on Dec. 10, 2020.

(51) Int. Cl.
| | |
|---|---|
| *C12N 7/00* | (2006.01) |
| *C12N 5/071* | (2010.01) |
| *C12N 15/86* | (2006.01) |

(52) U.S. Cl.
CPC ............. *C12N 7/00* (2013.01); *C12N 5/0686* (2013.01); *C12N 15/86* (2013.01); *C12N 2500/90* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS

| | | | |
|---|---|---|---|
| 6,165,782 A | 12/2000 | Naldini et al. | |
| 6,207,455 B1 | 3/2001 | Chang | |
| 6,218,181 B1 | 4/2001 | Verma et al. | |
| 6,277,633 B1 | 8/2001 | Olsen | |
| 6,323,031 B1 | 11/2001 | Cichutek | |

FOREIGN PATENT DOCUMENTS

| | | | | |
|---|---|---|---|---|
| CA | 3127629 A1 | 7/2020 | | |
| JP | 2005532779 A | 11/2005 | | |
| JP | 2014532414 A | 12/2014 | | |
| JP | 2016520329 A | 7/2016 | | |
| JP | 2017501740 A | 1/2017 | | |
| JP | 2018506283 A | 3/2018 | | |
| JP | 2018535682 A | 12/2018 | | |
| WO | WO-2005080556 A2 | 9/2005 | | |
| WO | WO-2007101130 A2 | 9/2007 | | |
| WO | WO-2020154607 A1 * | 7/2020 | ............ | C12M 29/10 |
| WO | WO-2020223274 A1 | 11/2020 | | |
| WO | WO-2022125793 A1 | 6/2022 | | |

OTHER PUBLICATIONS

Addgene "Science guides, adeno-associated virus (AAV) guide" Dec. 2, 2020 (Year: 2020).*
Holliday, "Choosing the right cell line for breast cancer" Breast Cancer Research, (Year: 2011).*
Kotin, "Large scale recombinant adeno-associated virus production" Human Molecular Genetics (Year: 2011).*
Maheshri et al., "Directed evolution of adeno-associated virus yields enhanced gene delivery vectors" Nature Biotechnology (Year: 2006).*
Nishimura et al., "Development of defective and persistant sendai virus vector: a unique gene delivery/expression system ideal for cell reprogramming" Journal of Biological Chemistry (Year: 2011).*
Wikipedia "Sleeping Beauty Transposon System" https://en.wikipedia.org/wiki/Sleeping_Beauty_transposon_system. Wayback Macine (Year: 2015).*
Walther et al., "Importance of interaction between integrin and actin cytoskeleton in suspension adaptation CHO cells" Appl Biochem Biotechnol (Year: 2016).*
Amado, R.G., and Chen, I.S., "Lentiviral vectors—the promise of gene therapy within reach?," Science 285(5428):674-676, American Association for the Advancement of Science, United States (Jul. 1999).
Apparailly, F., et al., "Adeno-associated virus pseudotype 5 vector improves gene transfer in arthritic joints," Hum Gene Ther 16(4):426-434, Mary Ann Liebert Inc., United States (Apr. 2005).
Bleckwenn, N.A., et al., "Production of recombinant proteins by vaccinia virus in a microcarrier based mammalian cell perfusion bioreactor," Biotechnol Bioeng 90(6):663-674, Wiley-VCH Verlag, Germany (Jun. 2005).
Chiorini, J.A., et al., "Cloning and characterization of adeno-associated virus type 5," J Virol 73(2):1309-1319, American Society for Microbiology, United States (Feb. 1999).
Federico, M., "Lentiviruses as gene delivery vectors," Curr Opin Biotechnol 10(5):448-453, Elsevier Ltd., United Kingdom (Oct. 1999).

(Continued)

*Primary Examiner* — Robert M Kelly
*Assistant Examiner* — John David Moore
(74) *Attorney, Agent, or Firm* — STERNE, KESSLER, GOLDSTEIN & FOX P.L.L.C.

(57) ABSTRACT

The disclosure is directed to a method for seed train expansion of adherent cells comprising culturing cells with a serum-supplemented growth medium in a N-2 vessel; removing the cells from the serum-supplemented medium; inoculating the cells from step into a serum-free growth medium in a N-1 vessel; culturing the cells in the N-1 vessel under suspension conditions; and inoculating a growth medium in a bioreactor with the suspension-cultured cells. In some aspects, the adherent cells are not suspension-adapted. In some aspects, the adherent cells are suspension-adapted. In some aspects, the adherent cells produced by the seed train expansion method are used to produce viral vectors. In some aspects, the viral vectors are AAV vectors.

32 Claims, 4 Drawing Sheets

(56)            References Cited

OTHER PUBLICATIONS

Goncalves, M., "Adeno-associated virus: from defective virus to effective vector," Virol J 2:43, BioMed Central Ltd., United Kingdom (May 2005).

International Search Report and Written Opinion for International Application No. PCT/US2021/062645, European Patent Office, Netherlands, mailed Apr. 4, 2022, 10 pages.

Malm, M., et al., "Evolution from adherent to suspension: systems biology of HEK293 cell line development," Sci Rep 10(1):18996, Nature Publishing Group, United Kingdom (Nov. 2020).

Mandel, R.J., and Burger, C., "Clinical trials in neurological disorders using AAV vectors: promises and challenges," Curr Opin Mol Ther 6(5):482-490, Thomson Scientific, United Kingdom (Oct. 2004).

Nathwani, A.C., et al., "Adenovirus-associated virus vector-mediated gene transfer in hemophilia B," N Engl J Med 365(25):2357-2365, Massachusetts Medical Society, United States (Dec. 2011).

Niemeyer, G.P., et al., "Long-term correction of inhibitor-prone hemophilia B dogs treated with liver-directed AAV2-mediated factor IX gene therapy," Blood 113(4):797-806, American Society of Hematology, United States (Jan. 2009).

Russell, W.C., "Update on adenovirus and its vectors," J Gen Virol 81(Pt 11):2573-2604, Microbiology Society, United Kingdom (Nov. 2000).

Simonelli, F., et al., "Gene therapy for Leber"s congenital amaurosis is safe and effective through 1.5 years after vector administration," Mol Ther 18(3):643-650, Cell Press, United States (Mar. 2010).

Vigna, E., and Naldini, L., "Lentiviral vectors: excellent tools for experimental gene transfer and promising candidates for gene therapy," J Gene Med 2(5):308-316, John Wiley and Sons Ltd., United States (Sep.-Oct. 2000).

Wang, C.Y., et al., "Improved neuronal transgene expression from an AAV-2 vector with a hybrid CMV enhancer/PDGF-beta promoter," J Gene Med 7(7):945-955, John Wiley and Sons Ltd., United States (Jul. 2005).

Gao, G., et al., "Clades of Adeno-associated viruses are widely disseminated in human tissues," J Virol 78(12):6381-6388, American Society for Microbiology, United States (Jun. 2004).

Martin, K.R., and Quigley, H.A., "Gene therapy for optic nerve disease," Eye (11):1049-1055, Springer Nature, Germany (Nov. 2004).

Mori, S., et al., "Two novel adeno-associated viruses from cynomolgus monkey: pseudotyping characterization of capsid protein," Virology 330(2):375-383, Elsevier, Netherlands (Dec. 2004).

Muzyczka, N., and Berns, K.I.,, "Parvoviridae: The Virus and Their Replication," in *Fields Virology*, 4th Edition, vol. 2, Knipe, D.M., and Howley, P., eds., Chapter 69, pp. 2327-2359, Lippincott-Raven Publishers, Philadelphia, United States (2001).

* cited by examiner

SUSPENSION MODE SEED TRAIN DEVELOPMENT FOR ADHERENT CELLS

RELATED APPLICATION

This application claims the benefit of U.S. Provisional Application No. 63/123,602, filed on Dec. 10, 2020. The entire teachings of the above-referenced application are incorporated by reference in their entirety.

BACKGROUND

Advances in the use of recombinant viral vectors for gene therapy and DNA vaccination applications have created a need for large-scale manufacture of clinical-grade viral vectors, such as adeno-associated virus (rAAV) vectors, for transfer of genetic materials.

Adherent mammalian cells containing a nucleic acid that encodes a recombinant protein are often cultured in large production bioreactors to produce therapeutic proteins of interest. Seed train processes are used to generate a sufficient number of such mammalian cells to inoculate the large production bioreactors. Conventional seed train processes start with the thawing of a cryopreserved cell bank vial, followed by multiple culturing steps (e.g., 5 or more) in progressively larger culture vessels. Conventional seed train processes have several disadvantages including the requirement for multiple manual manipulations during each step, which makes the whole process vulnerable to contamination and operator error. Particularly, the cell dissociation protocol for adherent cells during each passage often leads to contamination and makes the process unsuitable for scale-up production. These adherent seed train processes also do not allow for culturing high cell numbers necessary for achieving a desirable product yield in a sustainable and practical manner.

Suspension-adapted cell lines have been developed to attempt to overcome these issues. However, developing suspension-adapted cell lines is time consuming. Suspension-adapted cells also possess a different transcriptome than the parent adherent cell line. Therefore, there is a need for a new suspension system that permits a scale-up production of cells, e.g., the cells for viral production.

BRIEF SUMMARY

Some aspects of the disclosure are directed to a method of cell expansion comprising: (a) culturing cells with a first medium comprising serum in a N-2 container; (b) removing the cells from the first medium; (c) inoculating the cells from step (b) into a second medium comprising no serum or serum at a concentration less than the first medium in a N-1 container; (d) culturing the cells in the N-1 container under suspension conditions; and (e) inoculating a third medium in a bioreactor with the cells from step (d). In one embodiment, the second medium is a serum-free medium. In another embodiment, the second medium comprises the serum at a concentration less than the serum concentration in the first medium. In some aspects, the cells are adherent cells. In some aspects, the N-1 container and the N-2 container are the same. In some aspects, the N-1 container and the N-2 container are different. In some aspects, the N-1 container comprises a shake flask or a wave bag. In some aspects, the cells are passaged at least 1, at least 2, at least 3, at least 4, at least 5, or at least 6 times prior to step (e). In some aspects, the third medium comprises a higher serum concentration than the serum concentration in the second medium.

In some aspects, the adherent cells are selected from the group consisting of HeLa cells, CHO cells, HEK-293 cells, Sf9, Sf21, VERO cells, BHK cells, MDCK cells, MDBK cells, COS cells, and their derivatives. In some aspects, the adherent cells are human. In some aspects, the adherent cells are animal cells, insect cells, or larvae. In some aspects, the adherent cells are HeLa cells or HEK-293 cells. In some aspects, the adherent cells are HEK-293.

In some aspects, the adherent cells are not suspension-adapted. In some aspects, the adherent cells are suspension-adapted. In some aspects, culturing the cells under suspension conditions does not alter the adherent-dependency of the cells. In some aspects, the method does not alter the cells to create a new cell line. In some aspects, the method does not alter the cells genetically.

In some aspects, the method can further comprise culturing cells with the first medium in a N-3 container. In some aspects, the method can further comprise culturing cells with the first medium in a N-4 container. In some aspects, the method can further comprise culturing cells with the first medium in a N-5 container.

In some aspects, the bioreactor is an adherent bioreactor. In some aspects, the bioreactor is selected from the group consisting of a stirred tank bioreactor, a bubble column bioreactor, an airlift bioreactor, a fluidized bed bioreactor, a packed bed bioreactor, a photo-bioreactor bioreactor, and a fixed-bed bioreactor. In some aspects, the bioreactor is a fixed-bed bioreactor.

In some aspects, the third medium in the bioreactor comprises at least one factor which promotes cell adherence. In some aspects, the at least one factor which promotes cell adherence is selected from the group consisting of serum, FBS, fibronectin, collagen, laminin, calcium ions, proteoglycans or non-proteoglycan polysaccharides of the extracellular matrix; and combinations thereof. In some aspects, the third medium in the bioreactor comprises DMEM and 10% FBS.

In some aspects, the cells are cultured under suspension conditions for about 24-120 hours. In some aspects, the cells are cultured under suspension conditions for about 48-72 hours. In some aspects, the N-1 container is a shake flask. In some aspects, the N-1 container is a wave bag.

In some aspects, the method can further comprise contacting the cells with a first polynucleotide sequence in the bioreactor. In some aspects, the first polynucleotide sequence is a plasmid. In some aspects, the plasmid encodes a capsid protein of a recombinant viral particle selected from the group consisting of an AAV, a lentivirus, a herpes virus, a polyoma virus, and a vaccinia virus.

In some aspects, the viral particle is an AAV. In some aspects, the method can further comprise contacting the cells with a second polynucleotide encoding a transgene. In some aspects, the method comprises containing the cells with a third polynucleotide that encodes a helper gene. The first polynucleotide, in some embodiments, comprises one or more of an inverted terminal repeat, a nucleic acid encoding at least one AAV replication protein, a nucleic acid encoding at least one AAV packaging protein, a nucleic acid encoding at least one AAV structural capsid protein, or combinations thereof.

In some aspects, the method can further comprise culturing the cells in the bioreactor.

In some aspects, culturing comprises batch culturing. In some aspects, culturing comprises fed-batch culturing. In some aspects, culturing comprises perfusion culturing.

In some aspects, the cells are cultured under conditions which produce a recombinant viral particle.

Some aspects of the disclosure are directed to a method of cell expansion comprising: (a) culturing cells with a first medium comprising serum in a N-3 container; (b) removing the cells from the first medium; (c) inoculating the cells from step (b) into a second medium comprising no serum or serum at a concentration less than the first medium in a N-2 container; (d) culturing the cells in the N-2 container under suspension conditions; (e) and inoculating the cells from step (d) into the second medium in a N-1 container; (f) culturing the cells in the N-1 container under suspension conditions; and (g) inoculating a third medium in a bioreactor with the cells from step (d).

In some aspects, the cells are adherent cells. In some aspects, the N-1, the N-2, and the N-3 container are the same. In some aspects, the N-1, the N-2, and the N-3 container are different. In some aspects, the cells are passaged at least 1, at least 2, at least 3, at least 4, at least 5, or at least 6 times prior to step (g). In some aspects, the adherent cells are selected from the group consisting of HeLa cells, CHO cells, HEK-293 cells, Sf9, Sf21, VERO cells, BHK cells, MDCK cells, MDBK cells, COS cells and their derivatives. In some aspect, the adherent cells are human. In some aspect, the adherent cells are animal cells, insect cells, or larva. In some aspects, the adherent cells are HeLa cells or HEK-293 cells. In some aspects, the adherent cells are HEK-293.

In some aspects, the adherent cells are not suspension-adapted. In some aspects, the adherent cells are suspension-adapted. In some aspects, culturing the cells under suspension conditions does not alter the adherent-dependency of the cells. In some aspects, the method does not alter the cells to create a new cell line. In some aspects, the method does not alter the cells genetically.

In some aspects, the method can further comprise culturing cells with the first medium in a N-4 vessel. In some aspects, the method can further comprise culturing cells with the first medium in a N-5 container.

In some aspects, the bioreactor is an adherent bioreactor. In some aspects, the bioreactor is selected from the group consisting of a stirred tank bioreactor, a bubble column bioreactor, an airlift bioreactor, a fluidized bed bioreactor, a packed bed bioreactor, a photo-bioreactor bioreactor, and a fixed-bed bioreactor. In some aspects, the bioreactor is a fixed-bed bioreactor.

In some aspects, the third medium in the bioreactor comprises at least one factor which promotes cell adherence. In some aspects, the at least one factor which promotes cell adherence is selected from the group consisting of serum, FBS, fibronectin, collagen, laminin, calcium ions, proteoglycans or non-proteoglycan polysaccharides of the extracellular matrix; and combinations thereof. In some aspects, the third medium in the bioreactor comprises DMEM and 10% FBS.

In some aspects, the cells are cultured under suspension conditions for about 24-120 hours. In some aspects, the cells are cultured under suspension conditions for about 48-72 hours. In some aspects, the N2 container and the N-1 container is a shake flask. In some aspects, the N2 container and the N-1 container is a wave bag.

In some aspects, the method can further comprise contacting the cells with a first polynucleotide sequence in the bioreactor. In some aspects, the first polynucleotide sequence is a plasmid. In some aspects, the plasmid encodes a capsid protein of a recombinant viral particle selected from the group consisting of an AAV, a lentivirus, a herpes virus, a polyoma virus, and a vaccinia virus.

In some aspects, the viral particle is an AAV. In some aspects, the method can further comprise contacting the cells with a second polynucleotide sequence encoding a transgene. In some aspects, the first polynucleotide sequence comprises one or more of an inverted terminal repeat, a nucleic acid encoding at least one AAV replication protein, a nucleic acid encoding at least one AAV packaging protein, a nucleic acid encoding at least one AAV structural capsid protein, or combinations thereof.

In some aspects, the method can further comprise culturing the cells in the bioreactor.

In some aspects culturing comprises batch culturing. In some aspects, culturing comprises fed-batch culturing. In some aspects, culturing comprises perfusion culturing.

In some aspects, the cells are cultured under conditions which produce a recombinant viral particle.

Some aspects of the disclosure are directed to a method of cell expansion of adherent cells comprising: (a) culturing the adherent cells under adherent conditions in a first medium comprising serum; (b) removing the adherent cells from the first medium; (c) suspending the adherent cells in a second medium comprising no serum or serum at a concentration less than the first medium; (d) culturing the adherent cells from step c under suspension conditions; and (e) inoculating a third medium in a bioreactor with the adherent cells from step (d).

In some aspects, the method can further comprise passaging the adherent cells of step (a) at least once under adherent conditions. In some aspects, the method can further comprise passaging the adherent cells of step (d) at least one time under suspension conditions. In some aspects, the method can further comprise passaging the adherent cells of step (d) at least two, at least three, at least four, or at least five times under suspension conditions.

In some aspects, the bioreactor is an adherent bioreactor. In some aspects, the bioreactor is selected from the group consisting of a stirred tank bioreactor, a bubble column bioreactor, an airlift bioreactor, a fluidized bed bioreactor, a packed bed bioreactor, a photo-bioreactor bioreactor, and a fixed-bed bioreactor. In some aspects, the bioreactor is a fixed-bed bioreactor.

In some aspects, the adherent cells are not suspension-adapted. In some aspects, the adherent cells are suspension-adapted. In some aspects, culturing the cells under suspension conditions does not alter the adherent-dependency of the cells. In some aspects, the method does not alter the cells to create a new cell line. In some aspects, the method does not alter the cells genetically.

In some aspects, the third medium in the bioreactor comprises at least one factor which promotes cell adherence. In some aspects, the at least one factor which promotes cell adherence is selected from the group consisting of FBS, fibronectin, collagen, laminin, calcium ions, proteoglycans or non-proteoglycan polysaccharides of the extracellular matrix; and combinations thereof. In some aspects, the third medium in the bioreactor comprises DMEM and 10% FBS.

In some aspects, the adherent cells are passaged no more than two times under suspension conditions. In some aspects, the cells are passaged no more than more than three, no more than four, or no more than five times under suspension conditions. In some aspects, the cells are cultured under suspension conditions for about 24-120 hours. In some aspects, the adherent cells are grown under suspension conditions for 48-72 hours.

In some aspects, the adherent cells are selected from the group consisting of HeLa cells, CHO cells, HEK-293 cells, Sf9, Sf21, VERO cells, BHK cells, MDCK cells, MDBK cells, COS cells, and their derivatives. In some aspects, the adherent cells are human. In some aspects, the adherent cells are animal cells, insect cells, or larva. In some aspects, the adherent cells are HeLa cells or HEK-293 cells. In some aspects, the adherent cells are HEK-293 cells.

In some aspects, the method can further comprise contacting the adherent cells with a first polynucleotide sequence. In some aspects, the first polynucleotide sequence is a plasmid. In some aspects, plasmid encodes a capsid protein of a recombinant viral particle selected from the group consisting of an AAV, a lentivirus, a herpes virus, a polyoma virus, and a vaccinia virus.

In some aspects, the viral particle is an AAV. In some aspects, the method can further comprise contacting the adherent cells with a second polynucleotide sequence encoding a transgene. In some aspects, the first polynucleotide sequence comprises one or more of an inverted terminal repeat, a nucleic acid encoding at least one AAV replication protein, a nucleic acid encoding at least one AAV packaging protein, a nucleic acid encoding at least one AAV structural capsid protein, or combinations thereof.

In some aspects, the method can further comprise culturing the cells in the bioreactor.

In some aspects, culturing comprises batch culturing. In some aspects, culturing comprises fed-batch culturing. In some aspects, culturing comprises perfusion culturing.

In some aspects, the cells are cultured under conditions which produce a recombinant viral particle.

Some aspects of the disclosure are directed to a method of producing a viral vector, comprising: (a) culturing cells under adherent conditions in a first medium comprising serum; (b) removing the cells from the first medium; (c) suspending the cells in a second medium comprising no serum or serum at a concentration less than the first medium; (d) culturing the cells under suspension conditions; (e) inoculating a third medium in a bioreactor with the cells from step (d); (f) transfecting the cells with a polynucleotide encoding a viral particle; and (g) culturing the cells in the bioreactor under conditions in which the viral particle is produced. In one embodiment, the second medium is a serum-free medium.

In some aspects, the method can further comprise isolating the viral particle produced in step (g).

In some aspects, the polynucleotide is a plasmid. In some aspects, the viral particle is selected from the group consisting of an AAV, a lentiviral, a herpes virus, a polyoma virus, and a vaccinia virus. In some aspects, the viral particle is an AAV.

In some aspects, the bioreactor is an adherent bioreactor. In some aspects, the bioreactor is selected from the group consisting of a stirred tank bioreactor, a bubble column bioreactor, an airlift bioreactor, a fluidized bed bioreactor, a packed bed bioreactor, a photo-bioreactor bioreactor, and a fixed-bed bioreactor. In some aspects, the bioreactor is a fixed-bed bioreactor.

In some aspects, the third medium in the bioreactor comprises at least one factor which promotes cell adherence. In some aspects, the at least one factor which promotes cell adherence is selected from the group consisting of serum, FBS, fibronectin, collagen, laminin, calcium ions, proteoglycans or non-proteoglycan polysaccharides of the extracellular matrix; and combinations thereof. In some aspects, the third medium in the bioreactor comprises DMEM and 10% FBS.

In some aspects, the cells are adherent cells. In some aspects, the adherent cells are selected from the group consisting of HeLa cells, CHO cells, HEK-293 cells, Sf9, Sf21, VERO cells, BHK cells, MDCK cells, MDBK cells, COS cells, and their derivatives. In some aspects, the adherent cells are human. In some aspects, the adherent cells are animal cells, insect cells, or larva.

In some aspects, the adherent cells are HeLa cells or HEK-293 cells. In some aspects, the adherent cells are HEK-293.

In some aspects, the adherent cells are not suspension-adapted. In some aspects, the adherent cells are suspension-adapted. In some aspects, culturing the cells under suspension conditions does not alter the adherent-dependency of the cells. In some aspects, the method does not alter the cells to create a new cell line.

In some aspects, the method can further comprise passaging the cells of step (a) at least once under adherent conditions. In some aspects, the method can further comprise passaging the cells of step (d) at least one time under suspension conditions. In some aspects, the cells are passaged no more than two times under suspension conditions. In some aspects, the cells are passaged no more than two, no more than three, no more than four, or no more than five times under suspension conditions. In some aspects, the cells are grown under suspension conditions for about 24-120 hours. In some aspects, the cells are grown under suspension conditions for 48-72 hours.

In some aspects, culturing the cells in the bioreactor comprises batch culturing. In some aspects, culturing the cells in the bioreactor comprises fed-batch culturing. In some aspects, culturing the cells in the bioreactor comprises perfusion culturing.

BRIEF DESCRIPTION OF THE DRAWINGS/FIGURES

DETAILED DESCRIPTION

Definitions

Figure 1:
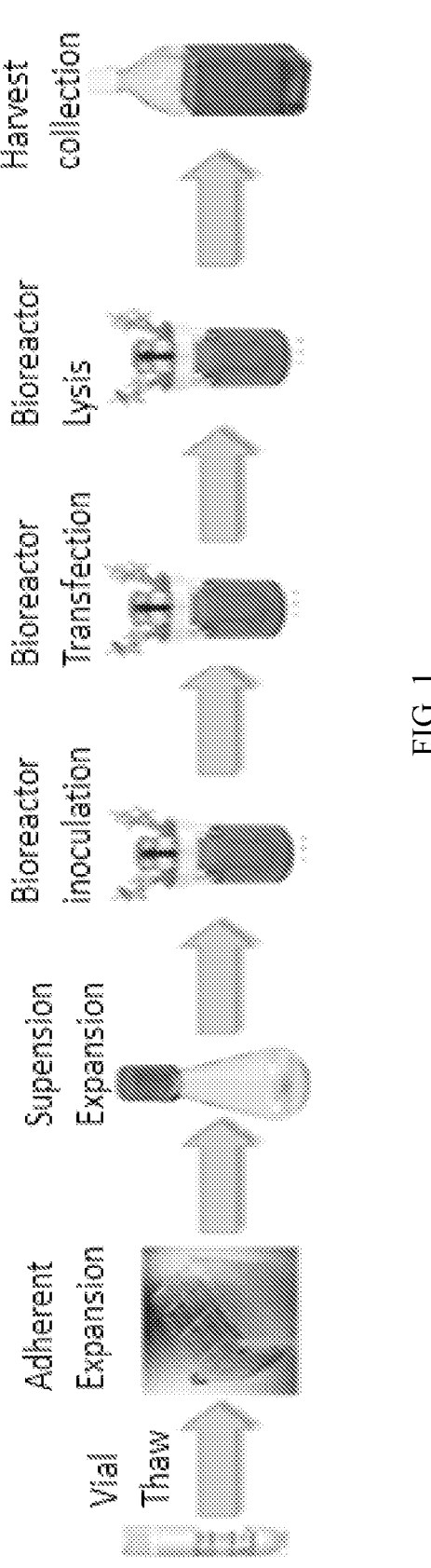
FIG. 1 is a visual representation of the hybrid seed-train expansion method as described herein.
Figure 2:
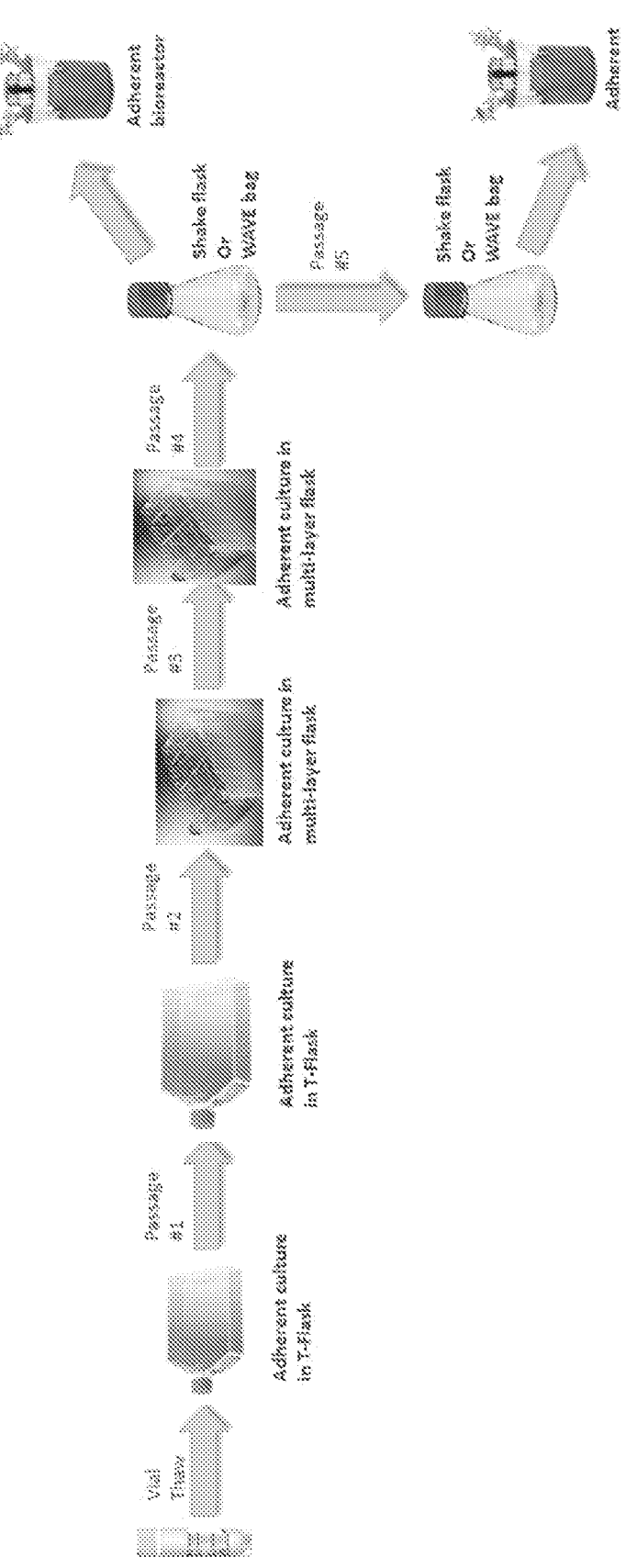
FIG. 2 is a visual representation of producing an AAV particle using the hybrid seed-train expansion method disclosed herein.

Unless defined otherwise, all technical and scientific terms used herein have the same meaning as commonly understood by one of ordinary skill in the art to which this disclosure belongs. In case of conflict, the present application, including the definitions, will control. Unless otherwise required by context, singular terms shall include pluralities and plural terms shall include the singular.

Throughout this disclosure, the term "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower), unless indicated otherwise.

The term "at least" prior to a number or series of numbers is understood to include the number adjacent to the term "at least," and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range. "At least" is also not limited to integers (e.g., "at least 5%" includes 5.0%, 5.1%, 5.18%) without consideration of the number of significant figures.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with, 37 CFR § 1.822 and established usage.

"Polynucleotide" or "nucleic acid" as used herein means a sequence of nucleotides connected by phosphodiester linkages. Polynucleotides are presented herein in the direction from the 5' to the 3' direction. A polynucleotide of the present disclosure can be a deoxyribonucleic acid (DNA) molecule or ribonucleic acid (RNA) molecule. Nucleotide bases are indicated herein by a single letter code: adenine (A), guanine (G), thymine (T), cytosine (C), inosine (I) and uracil (U).

As used herein, the term "polypeptide" encompasses both peptides and proteins, unless indicated otherwise.

The term "coding sequence" or sequence "encoding" is used herein to mean a DNA or RNA region (the transcribed region) which "encodes" a particular protein, e.g., such as an insulin or a glucokinase. A coding sequence is transcribed (DNA) and translated (RNA) into a polypeptide, in vitro or in vivo, when placed under the control of an appropriate regulatory region, such as a promoter. The boundaries of the coding sequence are determined by a start codon at the 5' (amino) terminus and a translation stop codon at the 3' (carboxy) terminus. A coding sequence can include, but is not limited to, cDNA from prokaryotes or eukaryotes, genomic DNA from prokaryotes or eukaryotes, and synthetic DNA sequences. A transcription termination sequence can be located 3' to the coding sequence.

A gene can comprise several operably linked fragments, such as a promoter, a 5' leader sequence, an intron, a coding sequence and a 3'-nontranslated sequence, e.g., comprising a polyadenylation site or a signal sequence. As used herein, "expression of a gene" refers to the process wherein a gene is transcribed into an RNA and/or translated into an active protein.

The term "promoter" is used herein to mean a nucleic acid sequence or fragment that functions to control the transcription of one or more genes (or coding sequence), located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most physiological and developmental conditions. An "inducible" promoter is a promoter that is regulated depending on physiological or developmental conditions. A "tissue specific" promoter is preferentially active in specific types of differentiated cells/tissues.

As used herein, the term "enhancer" is a cis-acting element that stimulates or inhibits transcription of adjacent genes. An enhancer that inhibits transcription is also referred to as a "silencer." Enhancers can function (e.g., can be associated with a coding sequence) in either orientation, over distances of up to several kilobase pairs (kb) from the coding sequence and from a position downstream of a transcribed region.

The terms "operatively linked," "operatively inserted," "operatively positioned," "under control" or "under transcriptional control" means that the promoter is in the correct location and orientation in relation to the nucleic acid to control RNA polymerase initiation and expression of the gene. The term "operably linked" means that a DNA sequence and a regulatory sequence(s) are connected in such a way as to permit gene expression when the appropriate molecules (e.g., transcriptional activator proteins) are bound to the regulatory sequence(s). The term "operably inserted" means that the DNA of interest introduced into the cell is positioned adjacent a DNA sequence which directs transcription and translation of the introduced DNA (i.e., facilitates the production of, e.g., a polypeptide encoded by a DNA of interest).

The term "transgene" is used herein to mean a gene or a nucleic acid molecule that is introduced into a cell. An example of a transgene is a nucleic acid encoding a therapeutic polypeptide. In some embodiments, the gene can be present, but in some cases normally not expressed or expressed at an insufficient level in the cell. In this context, "insufficient" means that although said gene is normally expressed in a cell, a condition and/or disease could still be developed. In certain aspects, the transgene allows for the increased expression or over-expression of the gene. The transgene can comprise sequences that are native to the cell, comprise sequences that do not naturally occur in the cell, or it can comprise combinations of both. In certain aspects, the transgene can comprise a sequence that can be operably linked to appropriate regulatory sequences for expression of the gene. In some aspects, the transgene is not integrated into the host cell's genome.

A "viral genome" or "vector genome" or "viral vector" refers to a sequence that comprises one or more polynucleotide regions encoding or comprising a molecule of interest, e.g., a protein, a peptide, and a polynucleotide or a plurality thereof. Viral vectors are used to deliver genetic materials into cells. Viral vectors can be modified for specific applications. In some aspects, the delivery vectors comprises a viral vector selected from the group consisting of an adeno-associated viral (AAV) vector, an adenoviral vector, a lentiviral vector, or a retroviral vector.

The term "adeno-associated virus vector" or "AAV vector" as used herein refers to any vector which comprises or derives from components of an adeno-associated vector and is suitable to infect mammalian cells, preferably human cells. The term AAV vector typically designates an AAV-type viral particle or virion comprising a payload. The AAV vector can be derived from various serotypes, including combinations of serotypes (i.e., "pseudotyped" AAV) or from various genomes (e.g., single stranded or self-complementary). In addition, the AAV vector can be replication defective and/or targeted. As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAVrh8, AAVrh10, AAVrh.74, snake AAV, avian AAV, bovine AAV, canine AAV, equine AAV, ovine AAV, goat AAV, shrimp AAV, those AAV serotypes and clades disclosed by Gao et al. (J. Virol. 78:6381 (2004)) and Moris et al. (Virol. 33:375 (2004)), and any other AAV. See, e.g., FIELDS et al. VIROLOGY, volume 2, chapter 69 (4th ed., Lippincott-Raven Publishers). In some aspects, an "AAV vector" includes a derivative of a known AAV vector. In some aspects, an "AAV vector" includes a modified or an artificial AAV vector. The terms "AAV genome" and "AAV vector" can be used interchangeably.

As used herein, an "AAV particle" is an AAV virus that comprises an AAV vector having at least one payload region (e.g., a polynucleotide encoding insulin and/or Gck) and at least one inverted terminal repeat (ITR) region. In some aspects, the terms "AAV vectors of the present disclosure" or "AAV vectors disclosed herein" refer to AAV vectors comprising a polynucleotide or nucleic acid disclosed herein encoding an insulin, a GcK, or a combination thereof, e.g., encapsulated in an AAV particle.

"Transduction" of a cell by a virus means that there is transfer of a nucleic acid from the virus particle to the cell. In some aspects, transduction refers to the delivery of a nucleic acid or nucleic acids encoding an insulin and/or a glucokinase into a recipient host cell by a viral vector. For example, transduction of a target cell by a rAAV vector of the disclosure leads to transfer of the rAAV genome (e.g., comprising a polynucleotide of the disclosure) contained in that vector into the transduced cell.

"Transfection" of a cell means that genetic material is introduced into a cell for the purpose of genetically modifying the cell. Transfection can be accomplished by a variety of means known in the art, e.g., transduction or electroporation.

"Vector" as used herein means a recombinant plasmid or virus that comprises a polynucleotide to be delivered into a host cell, either in vitro or in vivo.

"Recombinant" means distinct from that generally found in nature.

"Serotype" with respect to vector or virus capsid is defined by a distinct immunological profile based on the capsid protein sequences and capsid structure.

"AAV Cap" means AAV Cap proteins, VP1, VP2 and VP3 and analogs thereof.

"AAV Rep" means AAV Rep proteins and analogs thereof.

"Flanked," with respect to a sequence that is flanked by other elements, indicates the presence of one or more the flanking elements upstream and/or downstream, i.e., 5' and/or 3', relative to the sequence. The term "flanked" is not intended to indicate that the sequences are necessarily contiguous. For example, there may be intervening sequences between the nucleic acid encoding the transgene and a flanking element. A sequence (e.g., a transgene) that is "flanked" by two other elements (e.g., ITRs), indicates that one element is located 5' to the sequence and the other is located 3' to the sequence; however, there may be intervening sequences between.

As used herein, the term "gene therapy" is the insertion of nucleic acid sequences (e.g., a nucleic acid comprising a promoter operably linked to a polynucleotide encoding a therapeutic molecule as defined herein) into an individual's cells and/or tissues to treat a disease or condition. Gene therapy also includes insertion of a transgene that is inhibitory in nature, i.e., that inhibit, decrease or reduce expression, activity or function of an endogenous gene or protein, such as an undesirable or aberrant (e.g., pathogenic) gene or protein. Such transgenes can be exogenous. An exogenous molecule or sequence is understood to be molecule or sequence not normally occurring in the cell, tissue and/or individual to be treated. Both acquired and congenital diseases can be amenable to gene therapy.

The terms "media", "medium", "cell culture medium", "culture medium", "tissue culture medium", "tissue culture media", and "growth medium" as used herein refer to a solution containing nutrients which nourish growing cultured eukaryotic cells. Typically, these solutions provide essential and non-essential amino acids, vitamins, energy sources, lipids, and trace elements required by the cell for minimal growth and/or survival. The solution can also contain components that enhance growth and/or survival above the minimal rate, including hormones and growth factors. The solution is formulated to a pH and salt concentration optimal for cell survival and proliferation. The medium can also be a "defined medium" or "chemically defined medium"—a serum-free medium that contains no proteins, hydrolysates or components of unknown composition. Defined media are free of animal-derived components and all components have a known chemical structure. One of skill in the art understands a defined medium can comprise recombinant glycoproteins or proteins, for example, but not limited to, hormones, cytokines, interleukins and other signaling molecules.

The term "basal media formulation" or "basal media" as used herein refers to any cell culture media used to culture cells that has not been modified either by supplementation, or by selective removal of a certain component.

The terms "culture", "cell culture" and "eukaryotic cell culture" as used herein refer to a eukaryotic cell population, either surface-attached or in suspension that is maintained or grown in a medium under conditions suitable to survival and/or growth of the cell population. As will be clear to those of ordinary skill in the art, these terms as used herein can refer to the combination comprising the mammalian cell population and the medium in which the population is suspended.

The term "batch culture" as used herein refers to a method of culturing cells in which all the components that will ultimately be used in culturing the cells, including the medium as well as the cells themselves, are provided at the beginning of the culturing process. A batch culture is typically stopped at some point and the cells and/or components in the medium are harvested and optionally purified.

The term "fed-batch culture" as used herein refers to a method of culturing cells in which additional components are provided to the culture at some time subsequent to the beginning of the culture process. A fed-batch culture can be started using a basal medium. The culture medium with which additional components are provided to the culture at some time subsequent to the beginning of the culture process is a feed medium. The provided components typically comprise nutritional supplements for the cells which have been depleted during the culturing process. A fed-batch culture is typically stopped at some point and the cells and/or components in the medium are harvested and optionally purified.

The term "perfusion culture" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified.

"Growth phase" of the cell culture refers to the period of exponential cell growth (the log phase) where cells are generally rapidly dividing. During this phase, cells are cultured for a period of time, usually between 1-4 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. In some embodiments, during the growth phase, cells are cultured in nutrient medium containing the necessary additives generally at about 25°-40° C., in a humidified, controlled atmosphere, such that optimal growth is achieved for the particular cell line. In embodiments, cells are maintained in the growth phase for a period of about between one and seven days, e.g., between two to six days, e.g., six days. The length of the growth phase for the particular cells can be determined without undue experimentation. For example, the length of the growth phase will be the period of time sufficient to allow the particular cells to reproduce to a viable cell density within a range of about 20%-80% of the maximal possible viable cell density if the culture was maintained under the growth conditions. In some embodiments, "maximum growth rate" refers to the growth rate of the specific cell line/clone measured during its exponential growth phase, while the cells are in fresh culture medium (e.g., measured at a time during culture when nutrients are sufficient and there is not any significant inhibition of growth from any components of the culture).

The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

The term "cell density" as used herein refers to that number of cells present in a given volume of medium.

The term "cell derivative" or "derivative cell line" refers to a cell or cell line derived from, developed from, originating from, or arising out of an original cell line that varies in some respect from the original cell line, e.g., the derivative cell line can have one or more genetic modifications relative to the original cell line. The term "derivative cell line" does not imply any particular method or step to generate the cell line. In some aspects, multiple derivative cell lines can be attributed to a single original cell line.

Derivative cell lines, e.g., HEK-293 derivative cell lines derived from HEK-293 cells are contemplated for use in the methods described herein.

The term "bioreactor" or "culture vessel" as used herein refers to any vessel used for the growth of a mammalian cell culture. The bioreactor can be of any size so long as it is useful for the culturing of mammalian cells.

As used herein, the term "bioreactor run" can include one or more of the lag phase, log phase, or plateau phase growth periods during a cell culture cycle.

The term "N-1 culture vessel," "N-1 seed-train culture vessel," "N-1 vessel," "N1-culture," or "N1 container" as used herein refers to a culture vessel that is immediately before the N culture vessel (production culture vessel) and is used to grow the cell culture to a high viable cell density for subsequent inoculation into N (production) culture vessel. The cell culture to be grown in the N-1 culture vessel may be obtained after culturing the cells in several vessels prior to the N-1 culture vessel, such as N-6, N-5, N-4, N-3, and N-2 vessels. The terms "N culture vessel," "production culture vessel," "N vessel," "N bioreactor," or "production bioreactor" as used herein refers to the cell culture in the bioreactor after the N-1 bioreactor. The N culture is used in the production of the AAV.

The term "seeding" or "inoculating" as used herein refers to the process of providing a cell culture to a bioreactor or another vessel. In one embodiment, the cells have been propagated previously in another bioreactor or vessel. In another embodiment, the cells have been frozen and thawed immediately prior to providing them to the bioreactor or vessel. The term refers to any number of cells, including a single cell.

Hybrid Seed Train Expansion of Adherent Cells

Some aspects of the disclosure are related to a method of cell expansion comprising: (a) culturing cells with a first medium comprising serum in a N-2 container; (b) removing the cells from the first medium; (c) inoculating the cells from step (b) into a second medium comprising no serum or serum at a concentration less than the first medium in a N-1 container; (d) culturing the cells in the N-1 container under suspension conditions; and (e) inoculating a third medium in a bioreactor with the cells from step (d). In one embodiment, the second medium is a serum-free medium. In another embodiment, the second medium comprises the serum at a concentration less than the serum concentration in the first medium. In another embodiment, the third medium comprises serum at a concentration higher than the serum concentration in the second medium.

Some aspects of the disclosure are related to a method of seed-train expansion comprising (a) culturing cells with a first medium comprising serum in a N-3 container; (b) removing the cells from the first medium; (c) inoculating the cells from step (b) into a second medium comprising no serum or serum at a concentration less than the first medium in a N-2 container; (d) culturing the cells in the N-2 container under suspension conditions; (e) and inoculating the cells from step (d) into the second medium in a N-1 vessel; and (f) inoculating a third medium in a bioreactor with the cells from step (d). In one embodiment, the second medium is a serum-free medium. In another embodiment, the second medium comprises the serum at a concentration less than the serum concentration in the first medium. In another embodiment, the third medium comprises serum at a concentration higher than the serum concentration in the second medium.

Some aspects of the disclosure are related to a method of cell expansion of adherent cells comprising (a) culturing the adherent cells under adherent conditions in a first medium comprising serum; (b) removing the adherent cells from the first medium; (c) suspending the adherent cells in a second medium comprising no serum or serum at a concentration less than the first medium; (d) culturing the adherent cells under suspension conditions; and (e) inoculating a third medium in a bioreactor with the adherent cells from step (d). In some aspects, the method can further comprise passaging the adherent cells of step (a) at least once under adherent conditions. In some aspects, the method can further comprise further comprising passaging the adherent cells of step (d) at least one time under suspension conditions. In one embodiment, the second medium is a serum-free medium. In another embodiment, the second medium comprises the serum at a concentration less than the first medium in a N-1 container. In another embodiment, the third medium comprises serum at a concentration higher than the serum concentration in the second medium.

The first medium, second medium, and third medium can be any medium suitable for the particular cell being cultured. In some aspects, the medium contains e.g., inorganic salts, carbohydrates (e.g., sugars such as glucose, galactose, maltose or fructose), amino acids, vitamins (e.g., B group vitamins (e.g., B 12), vitamin A, vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates), hydrolysates (hydrolyzed proteins derived from plant or animal sources), and combinations thereof. The growth medium can be a commercially available media such as 5×-concentrated DMEM/F12 (Invitrogen), CD OptiCHO feed (Invitrogen), CD EfficientFeed (Invitrogen), Cell Boost (HyClone), BalanCD CHO Feed (Irvine Scientific), BD Recharge (Becton Dickinson), Cellvento Feed (EMD Millipore), Ex-cell CHOZN Feed (Sigma-Aldrich), CHO Feed Bioreactor Supplement (Sigma-Aldrich), SheffCHO (Kerry), Zap-CHO (Invitria), ActiCHO (PAA/GE Healthcare), Ham's F10 (Sigma), Minimal Essential Medium ([MEM], Sigma), RPMI-1640 (Sigma), and Dulbecco's Modified Eagle's Medium ([DMEM], Sigma). In some aspects, the first medium, second medium, and third medium can be a defined medium, as described herein. In some aspects, a defined medium can comprise DMEM and 10% FBS.

In some aspects, the serum-free growth second medium comprising no serum or serum at a concentration less than the first serum is substantially free (comprising no more than trace levels of) calcium ions, fetal bovine serum (FBS), fibronectin, collagen, laminin, or proteoglycans or non-proteoglycan polysaccharides of the extracellular matrix which would support the anchorage of cells. In one embodiment, the second medium is a serum-free medium. In another embodiment, the second medium comprises the serum at a concentration less than the serum concentration in the first medium.

In some aspects, the growth medium can have a pH of between about 6.5 and about 7.5, between about 6.5 and about 7.4, between about 6.5 and about 7.3, between about 6.5 and about 7.2, between about 6.5 and about 7.1, between about 6.5 and about 7.0, between about 6.5 and about 6.9, between about 6.5 and about 6.8, between about 6.5 and about 6.7, between about 6.6 and about 7.5, between about 6.6 and about 7.4, between about 6.6 and about 7.3, between about 6.6 and about 7.2, between about 6.6 and about 7.1, between about 6.6 and about 7.0, between about 6.6 and about 6.9, between about 6.6 and about 6.8, between about 6.7 and about 7.5, between about 6.7 and about 7.4, between about 6.7 and about 7.3, between about 6.7 and about 7.2, between about 6.7 and about 7.1, between about 6.7 and about 7.0, between about 6.7 and about 6.9, between about 6.8 and about 7.5, between about 6.8 and about 7.4, between about 6.8 and about 7.3, between about 6.8 and about 7.2, between about 6.8 and about 7.1, between about 6.8 and about 7.0, between about 6.9 and about 7.5, between about 6.9 and about 7.4, between about 6.9 and about 7.3, between about 6.9 and about 7.2, between about 6.9 and about 7.1, between about 7.0 and about 7.5, between about 7.0 and about 7.4, between about 7.0 and about 7.3, between about 7.0 and about 7.2, between about 7.1 and about 7.5, between about 7.1 and about 7.4, between about 7.1 and about 7.3, between about 7.2 and about 7.5, between about 7.2 and about 7.4, or between about 7.3 and about 7.5.

In some aspects, the cells can be cultured at a temperature of 32° C. to about 39° C., about 32° C. to about 37° C., between about 32° C. and about 37.5° C., between about 34° C. and about 37° C., between about 35° C. and about 37° C., between about 35.5° C. and about 37.5° C., between about 36° C. and about 37° C., or about 36.5° C. In some aspects, the cells can be incubated at a temperature of about 37° C. from the beginning to the end of the culturing period. In some aspects, the temperature can be changed or may vary slightly during the culturing period, e.g., on an hourly or daily basis. In some aspects, the temperature can be changed or shifted (e.g., increased or decreased) at about one day, two days, three days, four days, five days, six days, seven days, eight days, nine days, ten days, eleven days, twelve days, fourteen days, or fifteen days after the start of the culturing period, or at any time point within the culturing period. In some aspects, the temperature can be shifted upwards by about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0° C. In some aspects, the temperature can be shifted downwards by about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10° C.

In some aspects, the cell culture can be performed using an atmosphere containing about 1% to about 15% $CO_2$. In some aspects, cells can be cultured using an atmosphere containing about 14% $CO_2$, 12% $CO_2$, 10% $CO_2$, 8% $CO_2$, 6% $CO_2$, 5% $CO_2$, 4% $CO_2$, 3% $CO_2$, 2% $CO_2$, or about 1% $CO_2$.

In some aspects, the cell culture can be performed by maintaining a dissolved oxygen (dO2) in the cell culture of between about 3% and about 55%, between about 3% and about 50%, between about 3% and about 45%, between about 3% and about 40%, between about 3% and about 35%, between about 3% and about 30%, between about 3% and about 25%, between about 3% and about 20%, between about 3% and about 15%, between about 5% and about 55%, between about 5% and about 50%, between about 5% and about 45%, between about 5% and about 40%, between about 5% and about 35%, between about 5% and about 30%, between about 5% and about 25%, between about 5% and about 20%, between about 5% and about 15%, between about 5% and about 10%, between about 10% and about 55%, between about 10% and about 50%, between about 10% and about 45%, between about 10% and about 40%, between about 10% and about 35%, between about 10% and about 30%, between about 10% and about 25%, between about 10% and about 20%, between about 15% and about 55%, between about 15% and about 50%, between about 15% and about 45%, between about 15% and about 40%, between about 15% and about 35%, between about 15% and about 30%, between about 15% and about 25%, between about 15% and about 20%, between about 20% and about 55%, between about 20% and about 50%, between about 20% and about 45%, between about 20% and about 40%, between about 20% and about 35%, between about 20% and about 30%, between about 20% and about 25%, between about 25% and about 55%, between about 25% and about 50%, between about 25% and about 45%, between about 25% and about 40%, between about 25% and about 35%, between about 25% and about 30%, between about 30% and about 55%, between about 30% and about 50%, between about 30% and about 45%, between about 30% and about 40%, between about 30% and about 35%, between about 35% and about 55%, between about 35% and about 50%, between about 35% and about 45%, between about 35% and about 40%, between about 40% and about 55%, between about 40% and about 50%, between about 40% and about 45%, between about 45% and about 55%, between about 45% and about 50%, or between about 50% and about 55%.

In some aspects, the pH of the cell culture can be maintained at a specific pH value by the addition of a base solution, such as an alkali base solution. The pH of a cell culture can be maintained at a pH of between about 6.5 and about 7.5, between about 6.5 and about 7.4, between about 6.5 and about 7.3, between about 6.5 and about 7.2, between about 6.5 and about 7.1, between about 6.5 and about 7.0, between about 6.5 and about 6.9, between about 6.5 and about 6.8, between about 6.5 and about 6.7, between about 6.6 and about 7.5, between about 6.6 and about 7.4, between about 6.6 and about 7.3, between about 6.6 and about 7.2, between about 6.6 and about 7.1, between about 6.6 and about 7.0, between about 6.6 and about 6.9, between about 6.6 and about 6.8, between about 6.7 and about 7.5, between about 6.7 and about 7.4, between about 6.7 and about 7.3, between about 6.7 and about 7.2, between about 6.7 and about 7.1, between about 6.7 and about 7.0, between about 6.7 and about 6.9, between about 6.8 and about 7.5, between about 6.8 and about 7.4, between about 6.8 and about 7.3, between about 6.8 and about 7.2, between about 6.8 and about 7.1, between about 6.8 and about 7.0, between about 6.9 and about 7.5, between about 6.9 and about 7.4, between about 6.9 and about 7.3, between about 6.9 and about 7.2, between about 6.9 and about 7.1, between about 7.0 and about 7.5, between about 7.0 and about 7.4, between about 7.0 and about 7.3, between about 7.0 and about 7.2, between about 7.1 and about 7.5, between about 7.1 and about 7.4, between about 7.1 and about 7.3, between about 7.2 and about 7.5, between about 7.2 and about 7.4, or between about 7.3 and about 7.5

In some aspects, cell culture under suspension conditions can be done in any type of cell culture flask suitable for steady or mixed/shaken suspension cell expansion using for example a T-flask, roller bottle, spinner flask or shaker flask; or combinations thereof. In some aspects, the N-1 container is a shake flask. In some aspects, the N-1 container is a wave bag.

In some aspects, suspension conditions can include some form of agitation. In some aspects, the agitation can be rotary agitation. In some aspects, agitation can occur at a frequency of at about 25 RPM to about 500 RPM, between about 25 RPM and about 480 RPM, between about 25 RPM and about 460 RPM, between about 25 RPM and about 440 RPM, between about 25 RPM and about 420 RPM, between about 25 RPM and about 400 RPM, between about 25 RPM and about 380 RPM, between about 25 RPM and about 360

RPM, between about 25 RPM and about 340 RPM, between about 25 RPM and about 320 RPM, between about 25 RPM and about 300 RPM, between about 25 RPM and about 280 RPM, between about 25 RPM and about 260 RPM, between about 25 RPM and about 240 RPM, between about 25 RPM and about 220 RPM, between about 25 RPM and about 200 RPM, between about 25 RPM and about 180 RPM, between about 25 RPM and about 160 RPM, between about 25 RPM and about 140 RPM, between about 25 RPM and about 120 RPM, between about 25 RPM and about 100 RPM, between about 25 RPM and about 80 RPM, between about 25 RPM and about 60 RPM, between about 25 RPM and about 40 RPM, between about 25 RPM and about 35 RPM, between about 25 RPM and about 30 RPM, between about 50 RPM to about 500 RPM, between about 50 RPM and about 480 RPM, between about 50 RPM and about 460 RPM, between about 50 RPM and about 440 RPM, between about 50 RPM and about 420 RPM, between about 50 RPM and about 400 RPM, between about 50 RPM and about 380 RPM, between about 50 RPM and about 360 RPM, between about 50 RPM and about 340 RPM, between about 50 RPM and about 320 RPM, between about 50 RPM and about 300 RPM, between about 50 RPM and about 280 RPM, between about 50 RPM and about 260 RPM, between about 50 RPM and about 240 RPM, between about 50 RPM and about 220 RPM, between about 50 RPM and about 200 RPM, between about 50 RPM and about 180 RPM, between about 50 RPM and about 160 RPM, between about 50 RPM and about 140 RPM, between about 50 RPM and about 120 RPM, between about 50 RPM and about 100 RPM, between about 50 RPM and about 80 RPM, between about 50 RPM and about 60 RPM, between about 75 RPM to about 500 RPM, between about 75 RPM and about 480 RPM, between about 75 RPM and about 460 RPM, between about 75 RPM and about 440 RPM, between about 75 RPM and about 420 RPM, between about 75 RPM and about 400 RPM, between about 75 RPM and about 380 RPM, between about 75 RPM and about 360 RPM, between about 75 RPM and about 340 RPM, between about 75 RPM and about 320 RPM, between about 75 RPM and about 300 RPM, between about 75 RPM and about 280 RPM, between about 75 RPM and about 260 RPM, between about 75 RPM and about 240 RPM, between about 75 RPM and about 220 RPM, between about 75 RPM and about 200 RPM, between about 75 RPM and about 180 RPM, between about 75 RPM and about 160 RPM, between about 75 RPM and about 140 RPM, between about 75 RPM and about 120 RPM, between about 75 RPM and about 100 RPM, between about 75 RPM and about 80 RPM, between about 100 RPM to about 500 RPM, between about 100 RPM and about 480 RPM, between about 100 RPM and about 460 RPM, between about 100 RPM and about 440 RPM, between about 100 RPM and about 420 RPM, between about 100 RPM and about 400 RPM, between about 100 RPM and about 380 RPM, between about 100 RPM and about 360 RPM, between about 100 RPM and about 340 RPM, between about 100 RPM and about 320 RPM, between about 100 RPM and about 300 RPM, between about 100 RPM and about 280 RPM, between about 100 RPM and about 260 RPM, between about 100 RPM and about 240 RPM, between about 100 RPM and about 220 RPM, between about 100 RPM and about 200 RPM, between about 100 RPM and about 180 RPM, between about 100 RPM and about 160 RPM, between about 100 RPM and about 140 RPM, between about 100 RPM and about 120 RPM, between about 150 RPM to about 500 RPM, between about 150 RPM and about 480 RPM, between about 150 RPM and about 460 RPM, between about 150 RPM and about 440

RPM, between about 150 RPM and about 420 RPM, between about 150 RPM and about 400 RPM, between about 150 RPM and about 380 RPM, between about 150 RPM and about 360 RPM, between about 150 RPM and about 340 RPM, between about 150 RPM and about 320 RPM, between about 150 RPM and about 300 RPM, between about 150 RPM and about 280 RPM, between about 150 RPM and about 260 RPM, between about 150 RPM and about 240 RPM, between about 150 RPM and about 220 RPM, between about 150 RPM and about 200 RPM, between about 150 RPM and about 180 RPM, between about 150 RPM and about 160 RPM, between at about 200 RPM to about 500 RPM, between about 200 RPM and 480 RPM, between about 200 RPM and about 460 RPM, between about 200 RPM and about 440 RPM, between about 200 RPM and about 420 RPM, between about 200 RPM and about 400 RPM, between about 200 RPM and about 380 RPM, between about 200 RPM and about 360 RPM, between about 200 RPM and about 340 RPM, between about 200 RPM and about 320 RPM, between about 200 RPM and about 300 RPM, between about 200 RPM and about 280 RPM, between about 200 RPM and about 260 RPM, between about 200 RPM and about 240 RPM, between about 200 RPM and about 220 RPM, between about 240 RPM and about 500 RPM, between about 240 RPM and about 480 RPM, between about 240 RPM and about 460 RPM, between about 240 RPM and about 440 RPM, between about 240 RPM and about 420 RPM, between about 240 RPM and about 400 RPM, between about 240 RPM and about 380 RPM, between about 240 RPM and about 360 RPM, between about 240 RPM and about 340 RPM, between about 240 RPM and about 320 RPM, between about 240 RPM and about 300 RPM, between about 240 RPM and about 280 RPM, between about 240 RPM and about 260 RPM, between about 260 RPM and about 500 RPM, between about 260 RPM and about 480 RPM, between about 260 RPM and about 460 RPM, between about 260 RPM and about 440 RPM, between about 260 RPM and about 420 RPM, between about 260 RPM and about 400 RPM, between about 260 RPM and about 380 RPM, between about 260 RPM and about 360 RPM, between about 260 RPM and about 340 RPM, between about 260 RPM and about 320 RPM, between about 260 RPM and about 300 RPM, between about 260 RPM and about 280 RPM, between about 280 RPM and about 500 RPM, between about 280 RPM and about 480 RPM, between about 280 RPM and about 460 RPM, between about 280 RPM and about 440 RPM, between about 280 RPM and about 420 RPM, between about 280 RPM and about 400 RPM, between about 280 RPM and about 380 RPM, between about 280 RPM and about 360 RPM, between about 280 RPM and about 340 RPM, between about 280 RPM and about 320 RPM, between about 280 RPM and about 280 RPM, between about 300 RPM and about 500 RPM, between about 380 RPM and about 480 RPM, between about 380 RPM and about 460 RPM, between about 380 RPM and about 440 RPM, between about 380 RPM and about 420 RPM, between about 380 RPM and about 400 RPM, between about 400 RPM and about 500 RPM, between about 400 RPM and about 480 RPM, between about 400 RPM and about 460 RPM, between about 400 RPM and about 440 RPM, or between about 400 RPM and about 420 RPM. The agitation can be performed continuously or periodically.

In some aspects, the cells are passaged no more than two times under suspension conditions. In some aspects, the cells are passaged no more than three times under suspension conditions. In some aspects, the cells are passaged no more than four times under suspension conditions. In some aspects, the cells are passaged no more than five times under suspension conditions.

In some aspects, the cells are cultured in suspension culture for at least about 24 hours prior to a passage to an N-1 container. Accordingly, by way of example, where the cells are passaged five times under suspension conditions, the cells are cultured for at least about 24 hours in an N-5 container prior to a passage to an N-4 container; the cells are cultured for at least about 24 hours in an N-4 container prior to a passage to an N-3 container; the cells are cultured for at least about 24 hours in an N-3 container prior to a passage to an N-2 container; and the cells are cultured for at least about 24 hours in an N-2 container prior to a passage to an N-1 container.

In some aspects, the cells are cultured in suspension culture for about 24 to about 120 hours. In some aspects, the cells are cultured in suspension culture for about 24 to about 96 hours. In some aspects, the cells are cultured in suspension culture for about 36 to about 84 hours. In some aspects, the cells are cultured in suspension culture for about 48 to about 72 hours. In some aspects, the cells are cultured in suspension culture for about 54 to about 66 hours. In some aspects, the cells are cultured in suspension culture for about 24, about 30, about 36, about 42, about 48, about 54, about 60, about 66, about 72, about 78, about 84, about 90, or about 96 hours.

In some aspects of the disclosure, the cells are adherent cells. In some aspects, the adherent cells are HeLa cells, CHO cells, HEK-293 cells, Sf9, Sf21, VERO cells, BHK cells, MDCK cells, MDBK cells, COS cells, and their derivatives. In some aspects, the adherent cell is human. In some aspects, the adherent cells are animal cells, insect cells, or larva. In some aspects, the adherent cell is a HeLa or HEK-293 cell. In some aspects, the adherent cell is a HEK-293 cell.

In some aspects, suitable adherent cells comprise various commercially available HEK-293 cell line derivatives, including but not limited to: CRL 1573 (ATCC), 293-F (GIBCO), HEK 293T (ATCC), 293 H, 293 MSR, Expi293, Flp-In™-293, 293 Met (−), and T-REx™ 293. The HEK-293 cell line was immortalized by the integration of a 4 kbp adenoviral 5 (Ad5) genome fragment including the E1A and E1B genes, the expression of which enable continuous culturing of HEK293 cells by inhibiting apoptosis and interfering with transcription and cell cycle control pathways. (See Malm, M., *Sci Rep* 10, 18996 (2020)) herein incorporated by reference in its entirety). Certain HEK-293 cell line derivatives were established by genetic modification. One non-limiting example is the HEK293T derivative. The HEK293T genome contains the SV40 large T antigen, which enables production of recombinant proteins within plasmid vectors containing the SV40 promoter. Another non-limiting example is the HEK293MSR derivative. The HEK293MSR cell line is genetically modified to express the human macrophage scavenger receptor and strongly adheres to standard tissue culture plates. In some aspects of the present disclosure, suitable adherent cells are any of the commercially available genetically modified HEK-293 cell line derivatives.

In some aspects, the adherent cells are not suspension-adapted. In some aspects, culturing the cells under suspension conditions does not alter the adherent-dependency of the cells. In some aspects, the method does not alter the cells to create a new cell line. In some aspects, the method does not alter the cells genetically. The methods disclosed herein do not alter the genomic or transcriptomic profile of the cells. The methods disclosed herein do not alter the phenotype of the cell.

In some aspects, the cells are passaged multiple times under adherent conditions in serum-supplemented growth medium prior to inoculating the N-1 container. In some aspects, the cells are passaged at least 1 time, at least 2 times, at least 3 times, at least 4 times, at least 5 times, or at least 6 times under adherent conditions in serum-supplemented growth medium prior to inoculating the N-1 container. In some aspects, the cells are cultured in a N-2, N-3, N-4, N-5, N-6, N-7, N-8, N-9, or N-10 containers prior to inoculating the N-1 container. In some aspects, the cells are cultured in a N-3 and N-2 container. In some aspects, the cells are cultured in a N-4, N-3, and N-2 container. In some aspects, the cells are cultured in a N-6, N-5, N-4, N-3, and N-2 container. In some aspects, the cells are cultured in a N-6, N-5, N-4, N-3, N-2, and N-1 container. In some aspects, the N-6, N-5, N-4, N-3, N-2, and N-1 containers are the same. In some aspects, the N-6, N-5, N-4, N-3, N-2, and N-1 containers are different.

The N-1 container can comprise any type of N-1 container or cell culture container or vessel known in the art for maintaining a cell line prior to inoculation of a bioreactor, such as collapsible bags or flexible containers, non-collapsible or rigid containers, and any other configurations involving liquid containment. In some aspects, the N-1 container can be a shake flask. In some aspects, the N-1 container can be a wave bag.

In some aspects, the bioreactor is an adherent bioreactor. In some aspects, the bioreactor comprises at least one, more preferably a plurality of carriers onto which the expanded cells are intended to adhere, which may be either floating or fixed in the bioreactor. Preferably, said carriers can be made, for example, using polyethylene terephthalate, polystyrene, polyester, polypropylene, DEAE-dextran, collagen, glass, alginate or acrylamide. In some aspects, the bioreactor can be a bioreactor containing bead-type micro-carriers (e.g., Cytodex® brand beads, commercially available from GE Healthcare Inc. division of General Electric Corp.) or matrix type carriers (e.g., Fibra-Cell™ brand disks, commercially available from Eppendorf Corp.). In some aspects, the bioreactor uses a polyester fiber carrier such as that used in the iCELLis® nano or iCELLis® 500 bioreactors, (commercially available from Advanced Technology Materials Inc. (Brussels, Belgium) and Pall corporation (Fall River, Mass)).

In some aspects, the bioreactor can be any commercially available bioreactor for bioprocessing. In some aspects, the bioreactor can be a continuous stirred tank bioreactor. In some aspects, the bioreactor can be a bubble column bioreactor. In some aspects, the bioreactor can be an airlift bioreactor. In some aspects, the bioreactor can be a fluidized bed bioreactor. In some aspects, the bioreactor can be a packed bed bioreactor. In some aspects, the bioreactor can be a photo-bioreactor. In some aspects, the bioreactor can be a fixed-bed bioreactor. In one aspect, the bioreactor can be an ICELLIS fixed-bed bioreactor for manufacturing of viral vectors (Pall Corporation, Port Washington, NY).

In some aspects, the third medium in the bioreactor comprises at least one factor which promotes cell adherence. In some aspects, the at least one factor which promotes cell adherence is selected from the group consisting of FBS, fibronectin, collagen, laminin, calcium ions, proteoglycans or non-proteoglycan polysaccharides of the extracellular matrix; and combinations thereof. In some aspects, the at least one factor which promotes cell adherence can be added to the third medium just before, during, or after the inoculation of the suspension cells into bioreactor.

In some aspects the growth medium comprises DMEM and about 10% FBS by weight. In some aspects, the growth medium comprises about 2% to about 20% by weight FBS. In some aspects, the growth medium comprises about 3% to about 19% by weight of FBS. In some aspects, the growth medium comprises about 4% to about 18% by weight of FBS. In some aspects, the growth medium comprises about 5% to about 17% by weight of FBS. In some aspects, the growth medium comprises about 6% to about 16% by weight of FBS. In some aspects, the growth medium comprises about 7% to about 15% by weight of FBS. In some aspects, the growth medium comprises about 8% to about 14% by weight of FBS. In some aspects, the growth medium comprises about 9% to about 13% by weight of FBS. In some aspects, the growth medium comprises about 10% to about 12% by weight of FBS. In some aspects the growth medium comprises about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight of FBS.

In some aspects, the suspension expanded cells from step (d) can be inoculated directly into the bioreactor. In some aspects, the quantity of cells inoculated into the bioreactor varies based on the size of the bioreactor. In some aspects, a 4 m$^2$ bioreactor (e.g., iCELLis® nano bioreactor) is used. In some aspects, the 4 m$^2$ bioreactor is inoculated with between about $1\times10^8$ and $1\times10^9$ cells. In some aspects, the 4 m$^2$ bioreactor is inoculated with between about $3\times10^8$ and $7\times10^8$ cells, the 4 m$^2$ bioreactor is inoculated with between about $4\times10^8$ and $6\times10^8$ cells. the 4 m$^2$ bioreactor is inoculated with about $5\times10^8$ cells. In some aspects, equivalent cell densities are used for other size bioreactors.

In some aspects, the method of the disclosure can further comprise culturing the cells in the bioreactor. In some aspects, the cell culture comprises batch culturing. In some aspects, the cell culture comprises fed-batch culturing. In some aspects, the cell culture comprises perfusion culturing.

Fed-batch culturing includes the incremental (periodic) or continuous addition of a feed culture medium to an initial cell culture without substantial or significant removal of the growth medium from the cell culture. The cell culture in fed batch culturing can be disposed in a bioreactor (e.g., a production bioreactor, such as a 10,000-L production bioreactor). In some aspects, the feed culture medium can be the same as the growth medium. The feed culture medium can be either in a liquid form or a dry powder. In some aspects, the feed culture medium is a concentrated form of the growth medium and/or is added as a dry powder. In some aspects, both a first liquid feed culture medium and a different second liquid feed culture medium can be added (e.g., continuously added) to the growth medium. In some aspects, the addition of the first liquid feed culture medium and addition of the second liquid feed culture medium to the culture can be initiated at about the same time. In some aspects, the total volume of the first liquid feed culture medium and the second liquid feed culture medium added to the culture over the entire culturing period can be about the same.

When the feed culture medium is added continuously, the rate of addition of the feed culture medium can be held constant or can be increased (e.g., steadily increased) over the culturing period. A continuous addition of feed culture medium can start at a specific time point during the culturing period (e.g., when the cells reach a target viable cell density, e.g., a viable cell density of about $1\times10^6$ cells/mL, about $1.1\times10^6$ cells/mL, about $1.2\times10^6$ cells/mL, about $1.3\times10^6$ cells/mL, about $1.4\times10^6$ cells/mL, about $1.5\times10^6$ cells/mL, about $1.6\times10^6$ cells/mL, about $1.7\times10^6$ cells/mL, about $1.8\times10^6$ cells/mL, about $1.9\times10^6$ cells/mL, or about $2.0\times10^6$ cells/mL). In some aspects, the continuous addition of feed culture medium can be initiated at day 2, day 3, day 4, or day 5 of the culturing period.

In some aspects, an incremental (periodic) addition of feed culture medium can begin when the cells reach a target cell density (e.g., about $1\times10^6$ cells/mL, about $1.1\times10^6$ cells/mL, about $1.2\times10^6$ cells/mL, about $1.3\times10^6$ cells/mL, about $1.4\times10^6$ cells/mL, about $1.5\times10^6$ cells/mL, about $1.6\times10^6$ cells/mL, about $1.7\times10^6$ cells/mL, about $1.8\times10^6$ cells/mL, about $1.9\times10^6$, or about $2.0\times10^6$ cells/mL). In some aspects, incremental feed culture media addition can occur at regular intervals (e.g., every day, every other day, or every third day) or can occur when the cells reach specific target cell densities (e.g., target cell densities that increase over the culturing period). In some aspects, the amount of feed culture medium added can progressively increase between the first incremental addition of feed culture medium and subsequent additions of feed culture medium. In some aspects, the volume of a liquid culture feed culture medium added to the initial cell culture over any 24 hour period in the culturing period can be some fraction of the initial volume of the bioreactor containing the culture or some fraction of the volume of the initial culture.

In some aspects, the addition of the liquid feed culture medium (continuously or periodically) can occur at a time point that is between 6 hours and 7 days, between about 6 hours and about 6 days, between about 6 hours and about 5 days, between about 6 hours and about 4 days, between about 6 hours and about 3 days, between about 6 hours and about 2 days, between about 6 hours and about 1 day, between about 12 hours and about 7 days, between about 12 hours and about 6 days, between about 12 hours and about 5 days, between about 12 hours and about 4 days, between about 12 hours and about 3 days, between about 12 hours and about 2 days, between about 1 day and about 7 days, between about 1 day and about 6 days, between about 1 day and about 5 days, between about 1 day and about 4 days, between about 1 day and about 3 days, between about 1 day and about 2 days, between about 2 days and about 7 days, between about 2 days and about 6 days, between about 2 days and about 5 days, between about 2 days and about 4 days, between about 2 days and about 3 days, between about 3 days and about 7 days, between about 3 days and about 6 days, between about 3 days and about 5 days, between about 3 days and about 4 days, between about 4 days and about 7 days, between about 4 days and about 6 days, between about 4 days and about 5 days, between about 5 days and about 7 days, or between about 5 days and about 6 days, after the start of the culturing period.

In some aspects, the volume of a liquid feed culture medium added (continuously or periodically) to the initial cell culture over any 24 hour period can be between 0.01× and about 0.3× of the capacity of the bioreactor. The fraction may be between about 0.01× and about 0.28×, between about 0.01× and about 0.26×, between about 0.01× and about 0.24×, between about 0.01× and about 0.22×, between about 0.01× and about 0.20×, between about 0.01× and about 0.18×, between about 0.01× and about 0.16×, between about 0.01× and about 0.14×, between about 0.01× and about 0.12×, between about 0.01× and about 0.10×, between about 0.01× and about 0.08×, between about 0.01× and about 0.06×, between about 0.01× and about 0.04×, between about 0.02× and about 0.3×, between about 0.02× and about 0.28×, between about 0.02× and about 0.26×, between about 0.02× and about 0.24×, between about 0.02× and about 0.22×, between about 0.02× and about 0.20×, between about 0.02× and about 0.18×, between about 0.02× and about 0.16×, between about 0.02× and about 0.14×, between about 0.02× and about 0.12×, between about 0.02× and about 0.10×, between about 0.02× and about 0.08×, between about 0.02× and about 0.06×, between about 0.02× and about 0.05×, between about 0.02× and about 0.04×, between about 0.02× and about 0.03×, between about 0.025× and about 0.3×, between about 0.025× and about 0.28×, between about 0.025× and about 0.26×, between about 0.025× and about 0.24×, between about 0.025× and about 0.22×, between about 0.025× and about 0.20×, between about 0.025× and about 0.18×, between about 0.025× and about 0.16×, between about 0.025× and about 0.14×, between about 0.025× and about 0.12×, between about 0.025× and about 0.10×, between about 0.025× and about 0.08×, between about 0.025× and about 0.06×, between about 0.025× and about 0.04×, between about 0.05× and about 0.3×, between about 0.05× and about 0.28×, between about 0.05× and about 0.26×, between about 0.05× and about 0.24×, between about 0.05× and about 0.22×, between about 0.05× and about 0.20×, between about 0.05× and about 0.18×, between about 0.05× and about 0.16×, between about 0.05× and about 0.14×, between about 0.05× and about 0.12×, between about 0.05× and about 0.10×, between about 0.1× and about 0.3×, between about 0.1× and about 0.28×, between about 0.1× and about 0.26×, between about 0.1× and about 0.24×, between about 0.1× and about 0.22×, between about 0.1× and about 0.20×, between about 0.1× and about 0.18×, between about 0.1× and about 0.16× between about 0.1× and about 0.14×, between about 0.1×, between about 0.15× and about 0.3×, between about 0.15× and about 0.2×, between about 0.2× and about 0.3×, or between about 0.25× and about 0.3×, of the capacity of the bioreactor.

In some aspects, the volume of a liquid feed culture medium added (continuously or periodically) to the initial cell culture over any 24 hour period during the culturing period can be between 0.02× and about 1.0×, between about 0.02× and about 0.9×, between about 0.02× and about 0.8×, between about 0.02× and about 0.7×, between about 0.02× and about 0.6×, between about 0.02× and about 0.5×, between about 0.02× and about 0.4×, between about 0.02× and about 0.3×, between about 0.02× and about 0.2×, between about 0.02× and about 0.1×, between about 0.02× and about 0.08×, between about 0.02× and about 0.06×, between about 0.02× and about 0.05×, between about 0.02× and about 0.04×, between about 0.02× and about 0.03×, between about 0.05× and about 1.0×, between about 0.05× and about 0.8×, between about 0.05× and about 0.7×, between about 0.05× and about 0.6×, between about 0.05× and about 0.5×, between about 0.05× and about 0.4×, between about 0.05× and about 0.3×, between about 0.05× and about 0.2×, between about 0.05× and about 0.1×, between about 0.1× and about 1.0×, between about 0.1× and about 0.9×, between about 0.1× and about 0.8×, between about 0.1× and about 0.7×, between about 0.1× and about 0.6×, between about 0.1× and about 0.5×, between about 0.1× and about 0.4×, between about 0.1× and about 0.3×, between about 0.1× and about 0.2×, between about 0.2× and about 1.0×, between about 0.2× and about 0.9×, between about 0.2× and about 0.8×, between about 0.2× and about 0.7×, between about 0.2× and about 0.6×, between about 0.2× and about 0.5×, or between about 0.2× and about 0.4× of the volume of the initial cell culture.

In some aspects, the total amount of feed culture medium added (continuously or periodically) over the entire culturing period can be between about 1% and about 40% (e.g., between about 1% and about 35%, between about 1% and about 30%, between about 1% and about 25%, between about 1% and about 20%, between about 1% and about 15%, between about 1% and about 10%, between about 1% and about 5%, between about 1% and about 4%, between about 2% and about 40%, between about 2% and about 35%, between about 2% and about 30%, between about 2% and about 25%, between about 2% and about 20%, between about 2% and about 15%, between about 2% and about 10%, between about 2% and about 5%, between about 3% and about 40%, between about 3% and about 35%, between about 3% and about 30%, between about 3% and about 25%, between about 3% and about 20%, between about 3% and about 15%, between about 3% and about 10%, between about 3% and about 5%, between about 4% and about 40%, between about 4% and about 35%, between about 4% and about 30%, between about 4% and about 25%, between about 4% and about 20%, between about 4% and about 15%, between about 4% and about 10%, between about 4% and about 8%, between about 5% and about 40%, between about 5% and about 35%, between about 5% and about 30%, between about 5% and about 25%, between about 5% and about 20%, between about 5% and about 15%, between about 5% and about 10%, between about 10% and about 40%, between about 10% and about 35%, between about 10% and about 30%, between about 10% and about 25%, between about 10% and about 20%, between about 10% and about 15%, between about 15% and about 40%, between about 15% and about 35%, between about 15% and about 30%, between about 15% and about 25%, between about 15% and about 20%, between about 20% and about 40%, between about 20% and about 35%, between about 20% and about 30%, between about 20% and about 25%, between about 25% and about 40%, between about 25% and about 35%, between about 25% and about 30%, between about 30% and about 40%, between about 30% and about 35%, or between about 35% and about 40%) of the volume of the initial culture.

In some aspects, two different feed culture media are added (continuously or incrementally) during feed batch culturing. In some aspects, the amount or volume of the first feed culture medium and the second feed culture medium added can be substantially the same or can differ. In some aspects, the first feed culture medium can be in the form of a liquid and the second feed culture medium can be in the form of a solid. In some aspects, the first feed culture medium and the second feed culture medium can be liquid feed culture media.

Perfusion culturing comprises removing from the bioreactor a first volume of the growth medium, and adding to the production bioreactor a second volume of a second growth culture medium, wherein the first volume and the second volume are about equal. The cells are retained in the bioreactor by a cell retention device or through techniques, such as cell settling in a settling cone. In some aspects, the removal and addition of growth media can be performed simultaneously or sequentially, or some combination of the two. In some aspects, removal and addition can be performed continuously, such as at a rate that removes and replaces a volume of between 0.1% to 800%, between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, or between 4% and 30% of the capacity of the bioreactor.

In some aspects, the first volume of the first growth medium removed and the second volume of the second growth medium added can be held approximately the same over each 24-hour period. In some aspects, the rate at which the first volume of the first growth medium is removed (volume/unit of time) and the rate at which the second volume of the second growth medium is added (volume/unit of time) can be varied and, depends on the conditions of the particular cell culture system. In some aspects, the rate at which the first volume of the first growth medium is removed (volume/unit of time) and the rate at which the second volume of the second growth medium is added (volume/unit of time) can be about the same or can be different.

In some aspects, the volume removed and added can change by gradually increasing over each 24-hour period. In some aspects, the volume of the first growth medium removed and the volume of the second growth medium added within each 24-hour period can be increased over the culturing period. In some aspects, the volume can be increased by a volume that is between 0.5% to about 20% of the capacity of the bioreactor over a 24-hour period. In some aspects, the volume can be increased over the culturing period to a volume that is about 25% to about 150% of the capacity of the bioreactor or the first liquid culture medium volume over a 24-hour period.

In some aspects, after the first 48 to 96 hours of the culturing period, in each 24-hour period, the first volume of the first growth medium removed and the second volume of the second growth medium added is about 10% to about 95%, about 10% to about 20%, about 20% to about 30%, about 30% to about 40%, about 40% to about 50%, about 50% to about 60%, about 60% to about 70%, about 70% to about 80%, about 80% to about 90%, about 85% to about 95%, about 60% to about 80%, or about 70% of the volume of the first growth medium.

In some aspects, the first growth medium and the second growth medium can be the same type of media. In some aspects, the first growth medium and the second growth medium can be different. In some aspects, the second liquid culture medium may be more concentrated with respect to one or more media components.

In some aspects, the first volume of the first growth medium can be removed by using any automated system. In some aspects, alternating tangential flow filtration may be used. In some aspects, the first volume of the first growth medium can be removed by seeping or gravity flow of the first volume of the first growth medium through a sterile membrane with a molecular weight cut-off that excludes the cell. In some aspects, the first volume of the first growth medium can be removed by stopping or significantly decreasing the rate of agitation for a period of at least 1 minute, at least 2 minutes, 3 minutes, 4 minutes, 5 minutes, 10 minutes, 15 minutes, 20 minutes, 25 minutes, 30 minutes, 40 minutes, 50 minutes, or 1 hour, and removing or aspirating the first volume of the growth medium from the top of the production bioreactor.

In some aspects, the second volume of the second liquid culture medium can be added to the first liquid culture medium by a pump. In some aspects, the second liquid culture medium can be added to the first liquid medium manually, such as by pipetting or injecting the second volume of the second liquid culture medium directly onto the first liquid culture medium or in an automated fashion.

In some aspects, the method further comprises contacting the cells with a first polynucleotide sequence. In some aspects, the method further comprises transfecting the cells with a polynucleotide sequence. In some aspects, the polynucleotide sequence is a plasmid. In some aspects, the plasmid encodes a capsid protein of a recombinant viral particle selected from the group consisting of an AAV, a lentivirus, a herpes virus, a polyoma virus, and a vaccinia virus. In some aspects, the cells are transfected before they are inoculated into the bioreactor. In some aspects, the cells are transfected after they are inoculated into the bioreactor. In some aspects, the cells are contacted or transfected with a second polynucleotide and comprises a nucleic acid encoding a transgene. In some aspects, the cells are contacted or transfected with a third polynucleotide that encodes a helper gene. In one embodiment, the helper gene is an adenoviral help gene. In one embodiment, the first polynucleotide comprises one or more of an inverted terminal repeat, a nucleic acid encoding at least one AAV replication protein, a nucleic acid encoding at least one AAV packaging protein, or a nucleic acid encoding at least one AAV structural capsid protein.

In some aspects, the cells are cultured under conditions which produce the viral vector. In some aspects, the method further comprises isolating the produced viral vector.

In some aspects, the polynucleotide is a viral vector. In some aspects, the viral vector is an Adenoviral and Adeno-associated virus (AAV) vector. These vectors infect a wide number of dividing and non-dividing cell types including synovial cells and liver cells. The episomal nature of the adenoviral and AAV vectors after cell entry makes these vectors suited for therapeutic applications. (Russell, 2000, J. Gen. Virol. 81: 2573-2604; Goncalves, 2005, Virol J. 2(1): 43) as indicated above. AAV vectors can result in very stable long term expression of transgene expression (up to 9 years in dog (Niemeyer et al, Blood. 2009 Jan. 22; 113(4):797-806) and up to 2 years in human (Nathwani et al, N Engl J Med. 2011 Dec. 22; 365(25):2357-65, Simonelli et al, Mol Ther. 2010 March; 18(3):643-50. Epub 2009 Dec. 1.)). In some aspects, adenoviral vectors are modified to reduce the host response as reviewed by Russell (2000, supra). Method for gene therapy using AAV vectors are described by Wang et al., 2005, J Gene Med. March 9 (Epub ahead of print), Mandel et al., 2004, Curr Opin Mol Ther. 6(5):482-90, and Martin et al., 2004, Eye 18(11):1049-55, Nathwani et al, N Engl J Med. 2011 Dec. 22; 365(25):2357-65, Apparailly et al, Hum Gene Ther. 2005 April; 16(4):426-34.

In some aspects, the first polynucleotide sequence comprises one or more of an inverted terminal repeat, a nucleic acid encoding at least one AAV replication protein, a nucleic acid encoding at least one AAV packaging protein, a nucleic acid encoding at least one AAV structural capsid protein, or combinations thereof. In some aspects, the second polynucleotide comprises a nucleic acid encoding a transgene. In some aspects, the third polynucleotide encodes a helper gene.

In some aspects, the cells are cultured under conditions which produce a recombinant viral particle. In some aspects, the method further comprises isolating the produced recombinant viral particle.

In some aspects, the viral vector is a retroviral vector. In some aspects, the retroviral vector is a lentiviral based expression construct. Lentiviral vectors have the ability to infect and to stably integrate into the genome of dividing and non-dividing cells (Amado and Chen, 1999 Science 285:

674-6). Methods for the construction and use of lentiviral based expression constructs are described in U.S. Pat. Nos. 6,165,782, 6,207,455, 6,218,181, 6,277,633 and 6,323,031 and in Federico (1999, Curr Opin Biotechnol 10: 448-53) and Vigna et al. (2000, J Gene Med 2000; 2: 308-16).

In some aspects, the viral vector is a herpes virus vector, a polyoma virus vector or a vaccinia virus vector.

In some aspects, the viral vector comprises a transgene operably linked to appropriate regulatory sequences. The term "regulatory sequence" includes promoters, enhancers and other expression control elements (e.g., polyadenylation signals) that control the transcription or translation of the protein. Such regulatory sequences are described, for example, in Goeddel (Gene Expression Technology, Methods in Enzymology 185, Academic Press, San Diego, CA (1990)). In some aspects, the regulatory sequence can comprise a promoter sequence. In some aspects, the promoter sequence can be a cytomegalovirus (CMV) intermediate early promoter, viral long terminal repeat promoters (LTRs), such as those from murine moloney leukaemia virus (MMLV) rous sarcoma virus, or HTLV-1, the simian virus 40 (SV 40) early promoter or the herpes simplex virus thymidine kinase promoter. In some aspects, the promoter is a tissue specific promoter, including but not limited to, muscle, heart, CNS, and liver.

In some aspects, the viral vector includes a further nucleotide sequence coding for a further polypeptide. In some aspects, the further polypeptide can be a (selectable) marker polypeptide that allows for the identification, selection and/or screening for cells containing the viral vector. In some aspects, the marker polypeptide can be the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual (3$^{rd}$ edition), Cold Spring Harbor Laboratory, Cold Spring Harbor Laboratory Press, New York.

Production of Viral Vectors

Some aspects of the disclosure are directed to a method of producing a viral vector comprising expanding cells according to any one of the seed-train expansion methods disclosed herein, inoculating the growth medium in a bioreactor with the cells, transfecting the cells with a polynucleotide sequence encoding a viral particle, and culturing the cells in the bioreactor under conditions in which the viral particle is produced. In some aspects, the medium can be a defined medium or a conditioned medium. As used herein, the term "defined medium" or "defined media" or equivalents thereof refers to a biochemically defined formulation comprised solely of the biochemically defined constituents. In some embodiments, a defined medium includes solely constituents having known chemical compositions. In other embodiments, a defined medium includes constituents that are derived from known sources. For example, a defined medium can also include factors and other compositions secreted from known tissues or cells; however, the defined medium will not include the conditioned medium from a culture of such cells. Thus, a "defined medium" can, if indicated, include particular compounds added to form the culture medium. Defined media compositions are known in the art, for example, PCT/US2007/062755 and marketed as StemPro~hESC SFM by Invitrogen, Carlsbad, California, which is herein incorporated in its entirety. As used herein, the phrase "conditioned medium" refers to a medium that is altered as compared to a base medium. For example, the conditioning of a medium can cause molecules, such as nutrients and/or growth factors, to be added to or depleted from the original levels found in the base medium. In some embodiments, a medium is conditioned by allowing cells of certain types to be grown or maintained in the medium under certain conditions for a certain period of time.

The methods of introducing exogenous nucleic acid into host cells are well known in the art, and will vary with the host cell used. Techniques include, but are not limited to, dextran-mediated transfection, calcium phosphate precipitation, calcium chloride treatment, polyethylenimine mediated transfection, polybrene mediated transfection, protoplast fusion, electroporation, viral or phage infection, encapsulation of the polynucleotide(s) in liposomes, and direct microinjection of the DNA into nuclei. Transfection can be either transient or stable.

In some aspects, the polynucleotide sequence is a plasmid. In some aspects, the plasmid encodes a viral particle selected from the group consisting of an AAV, a lentiviral, a herpes virus, a polyoma virus, and a vaccinia virus. In some aspects, the polynucleotide sequence is a viral vector. In some aspects, the viral vector encodes a viral particle. In some aspects, the viral particle is selected from the group consisting of an AAV, a lentiviral, a herpes virus, a polyoma virus, and a vaccinia virus.

In some aspect, the disclosure provides a recombinant virus or viral vector produced by the methods described herein. In some embodiments, the recombinant virus or viral vector is of an AAV, a lentivirus, a herpes virus, a polyoma virus, or a vaccinia virus In some aspects, the viral vector is an AAV vector. In some aspects, the AAV vector can comprise a recombinant AAV vector (rAAV). A "rAAV vector" as used herein refers to a recombinant vector comprising part of an AAV genome encapsidated in a protein shell of capsid protein derived from an AAV serotype as disclosed herein. In some aspects, the AAV vector can comprise inverted terminal repeats (ITR) derived from an adeno-associated virus serotype, such as AAV1, AAV2, AAV3, AAV4, AAV5, AAV6, AAV7, AAV8, AAVrh8, AAV9, AAV10, AAVrh10, AAVrh74, AAV11, AAV12, and others.

Typically, a vector genome requires the use of flanking 5' and a 3' ITR sequences to allow for efficient packaging of the vector genome into the rAAV capsid. In some aspects, the rAAV genome present in a rAAV vector comprises at least the nucleotide sequences of the inverted terminal repeat regions (ITR) of one of the AAV serotypes, or nucleotide sequences substantially identical thereto, and nucleic acid sequence encoding a transgene under control of a suitable regulatory element (e.g., a promoter), wherein the regulatory element and modified nucleic acid sequence(s) are inserted between the two ITRs.

The complete genome of several AAV serotypes and corresponding ITR has been sequenced (Chiorini et al. 1999, J. of Virology Vol. 73, No. 2, p 1309-1319). They can be either cloned or made by chemical synthesis as known in the art, using for example an oligonucleotide synthesizer as supplied e.g. by Applied Biosystems Inc. (Fosters, Calif., USA) or by standard molecular biology techniques. The ITRs can be cloned from the AAV viral genome or excised from a vector comprising the AAV ITRs. The ITR nucleotide sequences can be either ligated at either end to the nucleotide sequence encoding one or more therapeutic proteins using standard molecular biology techniques, or the wild type AAV sequence between the ITRs can be replaced with the desired nucleotide sequence.

In some aspects, the viral capsid component of the packaged viral vectors can be a parvovirus capsid, e.g., AAV Cap and/or chimeric capsids. Examples of suitable parvovirus viral capsid components are capsid components from the family Parvoviridae, such as an autonomous parvovirus or a Dependovirus. For example, the viral capsid may be an AAV capsid (e.g., AAV1, AAV2, AAV3, AAV4, AAV5, AAV6, AAV7, AAV8, AAVRH8 AAV9, AAV10, AAVRH10, AAV11 or AAV12 capsid; one skilled in the art would know there are likely other variants not yet identified that perform the same or similar function), or may include components from two or more AAV capsids. A full complement of AAV Cap proteins includes VP1, VP2, and VP3. The ORF comprising nucleotide sequences encoding AAV VP capsid proteins can comprise less than a full complement AAV Cap proteins or the full complement of AAV Cap proteins can be provided.

In some aspects, one or more of the AAV Cap proteins can be a chimeric protein, including amino acid sequences AAV Caps from two or more viruses, preferably two or more AAVs. For example, the chimeric virus capsid can include an AAV1 Cap protein or subunit and at least one AAV2 Cap or subunit. In some aspects, the rAAV genome as present in a rAAV vector does not comprise any nucleotide sequences encoding viral proteins, such as the rep (replication) or cap (capsid) genes of AAV. In some aspects, the rAAV genome can further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art.

In some aspects, the rAAV genome as present in said rAAV vector can further comprise a promoter sequence operably linked to the nucleotide sequence encoding a transgene.

In some aspects, suitable 3' untranslated sequence can also be operably linked to the modified nucleic acid sequences encoding a transgene. Suitable 3' untranslated regions can be those naturally associated with the nucleotide sequence or can be derived from different genes, such as for example the bovine growth hormone 3' untranslated region (e.g., bGH polyadenylation signal, SV40 polyadenylation signal, SV40 polyadenylation signal and enhancer sequence).

Except as otherwise indicated, methods known to those skilled in the art may be used for the construction of recombinant parvovirus and AAV (rAAV) constructs, packaging vectors expressing the parvovirus Rep and/or Cap sequences, and transiently and stably transacted packaging cells. Such techniques are known to those skilled in the art. See, e.g., SAMBROOK et al., MOLECULAR CLONING: A LABORATORY MANUAL 2nd Ed. (Cold Spring Harbor, N.Y., 1989); AUSUBEL el al., CURRENT PROTOCOLS IN MOLECULAR BIOLOGY (Green Publishing Associates, Inc. and John Wiley Sons, Inc., New York).

In some aspects, the viral vector can be a lentiviral vector. Lentiviruses are complex retroviruses that in addition to the common retroviral genes gag, pol and env, contain other genes with regulatory or structural function. The higher complexity enables the lentivirus to modulate the life cycle thereof, as in the course of latent infection.

A typical lentivirus is the human immunodeficiency virus (HIV), the etiologic agent of AIDS. In vivo, HIV can infect terminally differentiated cells that rarely divide, such as lymphocytes and macrophages. In vitro, HIV can infect primary cultures of monocyte-derived macrophages (MDM) as well as HeLa-Cd4 or T lymphoid cells arrested in the cell cycle by treatment with aphidicolin or γ irradiation.

Infection of cells is dependent on the active nuclear import of HIV preintegration complexes through the nuclear pores of the target cells. That occurs by the interaction of multiple, partly redundant, molecular determinants in the complex with the nuclear import machinery of the target cell. Identified determinants include a functional nuclear localization signal (NLS) in the gag matrix (MA) protein, the karyophilic virion-associated protein, vpr, and a C-terminal phosphotyrosine residue in the gag MA protein.

The lentiviral genome and the proviral DNA have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA. However, the resulting mutant remains capable of directing the synthesis of all virion proteins.

In some aspects, the recombinant lentivirus is capable of infecting a non-dividing cell by transfecting a suitable host cell with two or more vectors carrying the packaging functions, namely gag, pol and env, as well as rev and tat. In some examples, vectors lacking a functional tat gene are desirable. Thus, for example, a first vector can provide a nucleic acid encoding a viral gag and a viral pol and another vector can provide a nucleic acid encoding a viral env to produce a packaging cell. Introducing a vector providing a heterologous gene, identified as a transfer vector, into that packaging cell yields a producer cell which releases infectious viral particles carrying the foreign gene of interest.

The gag, pol and env genes of the vectors of interest also are known in the art. Thus, the relevant genes are cloned into the selected vector and then used to transform the target cell of interest.

According to the above-indicated configuration of vectors and foreign genes, the second vector can provide a nucleic acid encoding a viral envelope (env) gene. The env gene can be derived from any virus, including retroviruses. The env preferably is an amphotropic envelope protein which allows transduction of cells of human and other species.

It may be desirable to target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific. Retroviral vectors can be made target-specific by inserting, for example, a glycolipid or a protein. Targeting often is accomplished by using an antigen-binding portion of an antibody or a recombinant antibody-type molecule, such as a single chain antibody, to target the retroviral vector. Those of skill in the art will know of, or can readily ascertain without undue experimentation, specific methods to achieve delivery of a retroviral vector to a specific target.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences, e.g., a promoter or enhancer. The regulatory sequence can be any eukaryotic promoter or enhancer, including for example, the Moloney murine leukemia virus promoter-enhancer element, the human cytomegalovirus enhancer or the vaccinia P7.5 promoter. In some cases, such as the Moloney murine leukemia virus promoter-enhancer element, the promoter-enhancer elements are located within or adjacent to the LTR sequences.

In some aspects, the lentiviral genome as present in said lentiviral vector further comprises a promoter sequence operably linked to the nucleotide sequence encoding a transgene. In some aspects, the promoter sequences are promoters which confer expression in muscle cells and/or muscle tissues. Examples of such promoters include a CMV and a RSV promoters as disclosed herein.

In some aspects, suitable 3' untranslated sequence can also be operably linked to the nucleic acid sequences encoding a transgene. Suitable 3' untranslated regions can be those naturally associated with the nucleotide sequence or can be derived from different genes, such as for example the bovine growth hormone 3' untranslated region (e.g., bGH polyadenylation signal, SV40 polyadenylation signal, SV40 polyadenylation signal and enhancer sequence).

In some aspects, additional nucleotide sequences can be operably linked to the nucleic acid sequence encoding a transgene, such as nucleotide sequences encoding signal sequences, nuclear localization signals, expression enhancers, and the like.

Except as otherwise indicated, methods known to those skilled in the art may be used for the construction of lentiviral constructs, vectors, and transiently and stably transacted packaging cells. Such techniques are known to those skilled in the art. See, e.g., SAMBROOK et al., MOLECULAR CLONING: A LABORATORY MANUAL 2nd Ed. (Cold Spring Harbor, N.Y., 1989); AUSUBEL el al., CURRENT PROTOCOLS IN MOLECULAR BIOLOGY (Green Publishing Associates, Inc. and John Wiley Sons, Inc., New York).

In some aspects, the method further comprises isolating the produced viral particle. The viral vector replicates inside the cell and is thereby amplified and produces viral particles. Viral infection results in the lysis of the transfected cells. The lytic characteristics of viral vectors such as, AAV, therefore permits two different modes of virus particle production and isolation. The first mode is harvesting virus particles prior to cell lysis, employing external factors to lyse the cells. The second mode is harvesting virus particles from supernatant after almost complete cell lysis by the produced virus.

Methods that can be used for active cell lysis are known to the person skilled in the art. In some aspects, cells can be lysed by freeze-thaw, solid shear, hypertonic and/or hypotonic lysis, liquid shear, sonication, high-pressure extrusion, detergent lysis, combinations of the above, and the like.

In some aspects, the cells can be lysed using at least one detergent. In some aspects, the detergent can include anionic, cationic, zwitterionic, and nonionic detergents. In some aspects, the concentration of the detergent can be about 0.1%-5% (w/w). In some aspects, the detergent can be Triton X-100.

In some aspects, nuclease can be employed to remove contaminating nucleic acids, i.e., native nucleic acids from transfected cells. In some aspects, the nuclease can be BENZONASE®, PULMOZYME®, or any other DNase and/or RNase commonly used within the art.

Methods for harvesting or isolating viral vectors from transfected cells have been extensively disclosed in WO 2005/080556, which is incorporated herein by reference in its entirety.

In some aspects, the time of harvest or isolation of the viral vector is between about 24 and 120 hours post transfection, between about 36 and 108 hours, between about 48 and about 96 hours post transfection, between about 60 and about 84 hours post transfection. In some aspects, the time of harvest or isolation of the vector is about 72 hours post transfection.

In some aspects, the isolated viral particle can be further purified. In some aspects, purification of the viral particles can be performed in several steps comprising clarification, ultrafiltration, diafiltration or separation with chromatography. Such methods have been described in WO 2005/080556, incorporated herein by reference in its entirety. In some aspects, clarification may be done by a filtration step, removing cell debris and other impurities from the cell lysate. In some aspects, ultrafiltration is used to concentrate the virus solution. In some aspects, diafiltration, buffer exchange, or ultrafilters can be used to remove and exchange salts, sugars and the like. The person skilled in the art knows how to find the optimal conditions for each purification step.

In some aspects, purification can be achieved by density gradient centrifugation. In some aspects, purification employs at least one chromatography step. In some aspects, the viral vector can be purified by anion exchange chromatography, size exclusion chromatography, or a combination thereof.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

WORKING EXAMPLES

HEK 293 cells were passaged four times in adherent conditions. Before going into the penultimate expansion culture, the cells were harvested and centrifuged to wash away serum (@300 g for 5 minutes), and resuspended in serum-free growth medium (EXPI293) in suspension shake flasks at a seeding density of 0.5+E6 cells/mL. They were then allowed to grow and expand in numbers for 48-72 hours. The suspension cells were then collected and inoculated in shake flasks or WAVE bags, depending on how many viable cells were required for bioreactor inoculation. At the end of 72 hours, the concentrations of viable cells were determined using cell counting equipment. Then the necessary volume containing preferred total viable cells was added to the adherent bioreactor containing DMEM and 10% FBS. Additional FBS was appropriately added to account for the addition of serum-free suspension culture volume so that the final FBS concentration was maintained at 10%.

Figures 3A, 3B:
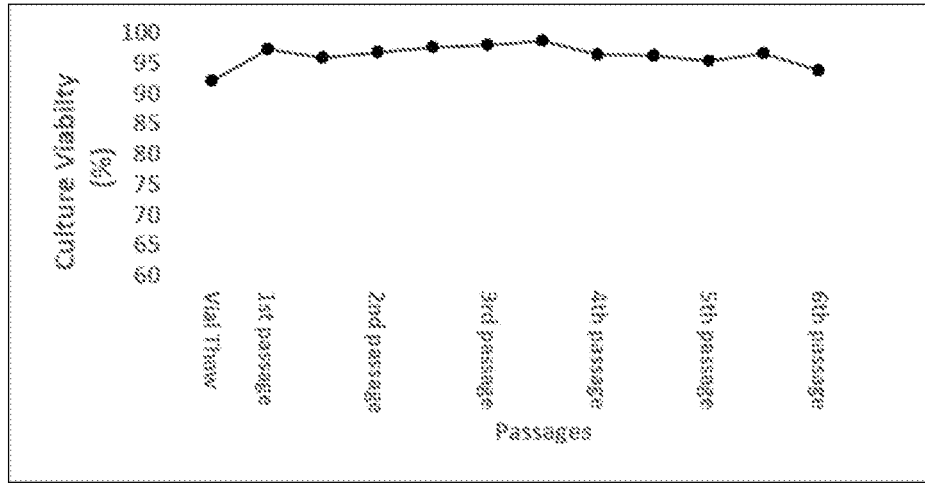
FIG. 3A is a graph showing the viability of HEK293 cells cultured according the hybrid seed-train expansion method disclosed herein.
FIG. 3B is a graph showing the viability of HEK293 cells cultured under adherent conditions only.
Figure 4A:
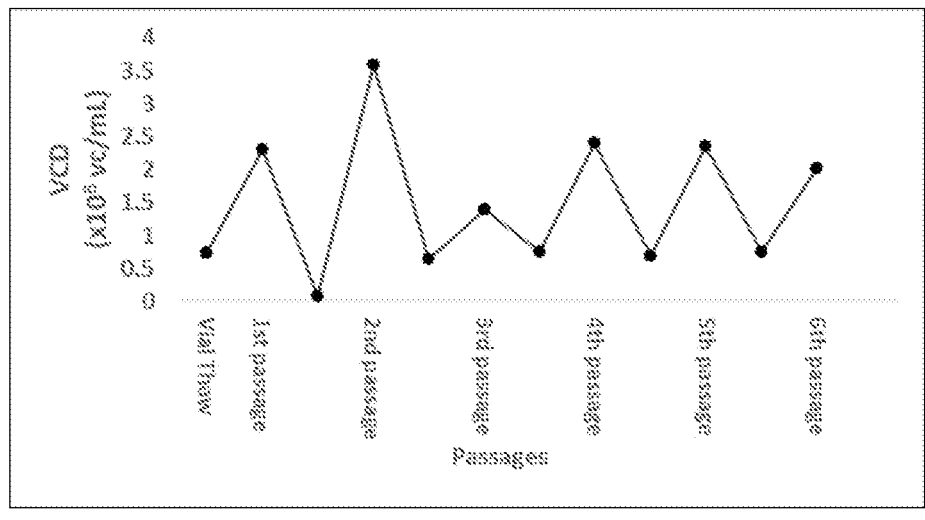
FIG. 4A is a graph showing the viable cell density of HEK293 cells cultured according to the hybrid seed-train expansion method disclosed herein.
Figure 4B:
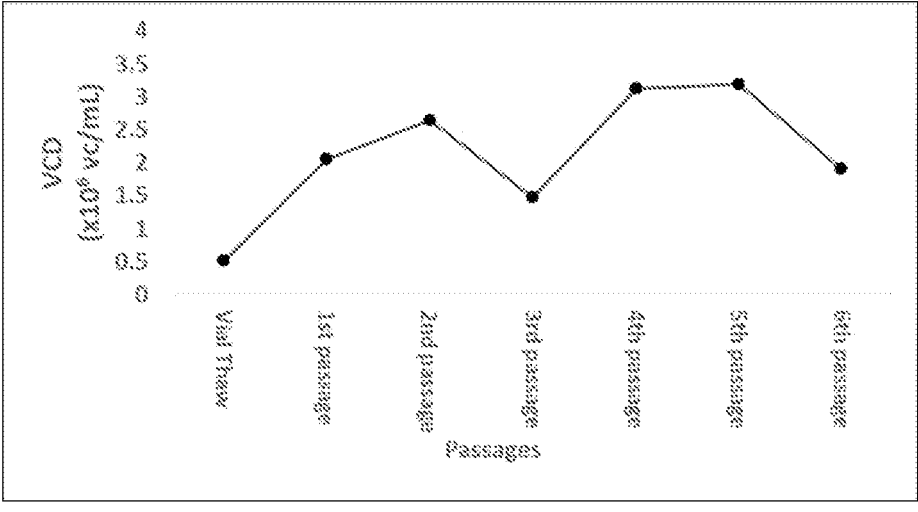
FIG. 4B is a graph showing the viable cell density of HEK293 cells cultured under adherent conditions only.

As shown in FIG. 3, the cell viabilities in both seed train and adherent systems were similar. With respect to viable cell density (VCD), in the hybrid seed train system, the VCD after 6th passage was higher than the one after 1st passage (FIG. 4A), which is comparable to the adherent system (FIG. 4B). In the meantime, the seed train system, with suspension or suspension adapted cells, permitted a more convenient passage than the traditional adherent system. Also, the cell passage in the seed train system with suspension cell culture avoids usage of trypsin, and minimizes contamination, thus allowing a scale-up production or manufacture of therapeutical viral vectors.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of cell expansion of adherent mammalian cells comprising:
   (a) culturing the adherent mammalian cells under adherent conditions with a first growth medium comprising serum in a N-2 container;
   (b) removing the adherent mammalian cells from the first growth medium;
   (c) inoculating the adherent mammalian cells from step (b) into a second growth medium comprising no serum or serum at a concentration less than the first growth medium in a N-1 container;
   (d) culturing the adherent mammalian cells in the N-1 container under suspension conditions in the second growth medium;
   (e) collecting the adherent mammalian cells or the adherent mammalian cells in the second growth medium from step (d) from the N-1 container;
   (f) passaging the adherent mammalian cells from step (d) at least one time under suspension conditions in the second growth medium;

(g) inoculating the adherent mammalian cells or the adherent mammalian cells in the second growth medium with a third growth medium in a bioreactor; and (h) culturing the adherent mammalian cells in the bioreactor.

2. The method of claim 1, wherein the third growth medium comprises a higher serum concentration than the serum concentration in the second growth medium.

3. The method of claim 1, wherein the adherent mammalian cells are Hela cells, CHO cells, HEK-293 cells, VERO cells, BHK cells, MDCK cells, MDBK cells, or COS cells.

4. The method of claim 1, further comprising culturing the adherent mammalian cells with the first growth medium in a N-3 container.

5. The method of claim 4, further comprising culturing the adherent mammalian cells with the first growth medium in a N-4 container.

6. The method of claim 5, further comprising culturing the adherent mammalian cells with the first growth medium in a N-5 container.

7. The method of claim 1, wherein the third growth medium in the bioreactor comprises at least one factor which promotes cell adherence.

8. The method of claim 7, wherein the at least one factor which promotes cell adherence is serum, FBS, fibronectin, collagen, laminin, calcium ions, proteoglycans or non-proteoglycan polysaccharides of the extracellular matrix, or combinations thereof.

9. The method of claim 8, wherein the third growth medium in the bioreactor comprises DMEM and 10% FBS.

10. The method of claim 1, further comprising contacting the adherent mammalian cells with a first polynucleotide sequence in the bioreactor.

11. The method of claim 10, wherein the first polynucleotide sequence is a plasmid.

12. The method of claim 10, further comprising contacting the adherent mammalian cells with a second polynucleotide encoding a transgene.

13. The method of claim 12, further comprising contacting the adherent mammalian cells with a third polynucleotide that encodes an adenoviral helper gene.

14. A method of cell expansion of adherent mammalian cells comprising:

(a) culturing the adherent mammalian cells under adherent conditions with a first growth medium comprising serum in a N-3 container;

(b) removing the adherent mammalian cells from the first growth medium;

(c) inoculating the adherent mammalian cells from step (b) into a second growth medium comprising no serum or serum at a concentration less than the first growth medium in a N-2 container;

(d) culturing the adherent mammalian cells in the N-2 container under suspension conditions in the second growth medium;

(e) collecting the adherent mammalian cells or the adherent mammalian cells in the second growth medium from step (d) from the N-2 container;

(f) inoculating the adherent mammalian cells or the adherent mammalian cells in the second growth medium into the second growth medium in a N-1 container;

(g) culturing the adherent mammalian cells in the N-1 container under suspension conditions in the second growth medium;

(h) collecting the adherent mammalian cells or the adherent mammalian cells in the second growth medium from step (g) from the N-1 container;

(i) inoculating the adherent mammalian cells or the adherent mammalian cells in the second growth medium with a third growth medium in a bioreactor; and (j) culturing the adherent mammalian cells in the bioreactor.

15. The method of claim 14, further comprising culturing the adherent mammalian cells with the first growth medium in a N-4 container.

16. The method of claim 15, further comprising culturing the adherent mammalian cells with the first growth medium in a N-5 container.

17. A method of seed-train expansion of adherent mammalian cells comprising:

(a) culturing the adherent mammalian cells under adherent conditions in a first growth medium comprising serum;

(b) removing the adherent mammalian cells from the first growth medium;

(c) suspending the adherent mammalian cells in a second growth medium comprising no serum or serum at a concentration less than the first growth medium;

(d) culturing the adherent mammalian cells from step (c) under suspension conditions in the second growth medium;

(e) passaging the adherent mammalian cells from step (d) at least one time under suspension conditions in the second growth medium;

(f) inoculating the adherent mammalian cells or the adherent mammalian cells in the second growth medium with a third growth medium in a bioreactor; and (g) culturing the adherent mammalian cells in the bioreactor.

18. The method of claim 17, wherein the adherent mammalian cells of step (a) are passaged at least once under adherent conditions.

19. The method of claim 17, wherein the adherent mammalian cells are passaged no more than two times under suspension conditions.

20. A method of producing a viral particle, comprising:

(a) culturing adherent mammalian cells under adherent conditions in a first growth medium comprising serum;

(b) removing the adherent mammalian cells from the first growth medium;

(c) suspending the adherent mammalian cells in a second growth medium comprising no serum or serum at a concentration less than the first growth medium;

(d) culturing the adherent mammalian cells from step (c) under suspension conditions in the second growth medium;

(e) passaging the adherent mammalian cells from step (d) at least one time under suspension conditions in the second growth medium;

(f) inoculating the adherent mammalian cells or the adherent mammalian cells in the second growth medium with a third growth medium in a bioreactor;

(g) transfecting the adherent mammalian cells with a polynucleotide sequence encoding a viral capsid protein; and (h) culturing the adherent mammalian cells in the bioreactor under conditions in which the viral particle is produced.

21. The method of claim 20, further comprising isolating the viral particle produced in step (h).

22. The method of claim 20, wherein the adherent mammalian cells of step (a) are passaged at least once under adherent conditions.

23. The method of claim 20, wherein the adherent mammalian cells of step (e) are passaged at least two, at least three, at least four, or at least five times under suspension conditions.

24. The method of claim 11, wherein the plasmid encodes a capsid protein of a recombinant AAV particle.

25. The method of claim 24, wherein the adherent mammalian cells are cultured under conditions which produce the recombinant AAV particle.

26. The method of claim 1, wherein the adherent mammalian cells of step (f) are passaged at least two times under suspension conditions before being inoculated in the bioreactor.

27. The method of claim 14, wherein the adherent mammalian cells of step (g) are passaged at least one time under suspension conditions before being inoculated in the bioreactor.

28. The method of claim 17, wherein the adherent mammalian cells of step (e) are passaged at least two times under suspension conditions before being inoculated in the bioreactor.

29. The method claim 1, wherein the bioreactor is an adherent bioreactor.

30. The method of claim 14, wherein the bioreactor is an adherent bioreactor.

31. The method of claim 17, wherein the bioreactor is an adherent bioreactor.

32. The method of claim 20, wherein the bioreactor is an adherent bioreactor.

\* \* \* \* \*